(12) United States Patent
Teichberg

(10) Patent No.: US 9,422,609 B2
(45) Date of Patent: Aug. 23, 2016

(54) METHODS, COMPOSITIONS AND DEVICES FOR MAINTAINING CHEMICAL BALANCE OF CHLORINATED WATER

(75) Inventor: Vivian I. Teichberg, Savyon (IL)

(73) Assignees: Mia Levite, Savyon (IL); Yaar Teichberg, Savyon (IL); Nof Lyle Teichberg, Savyon (IL)

( * ) Notice: Subject to any disclaimer, the term of this patent is extended or adjusted under 35 U.S.C. 154(b) by 1044 days.

(21) Appl. No.: 12/225,180

(22) PCT Filed: Mar. 14, 2007

(86) PCT No.: PCT/IL2007/000336
§ 371 (c)(1),
(2), (4) Date: Sep. 16, 2008

(87) PCT Pub. No.: WO2007/107981
PCT Pub. Date: Sep. 27, 2007

(65) Prior Publication Data
US 2010/0270228 A1    Oct. 28, 2010

Related U.S. Application Data

(60) Provisional application No. 60/783,028, filed on Mar. 17, 2006.

(51) Int. Cl.
    *C12N 9/78*    (2006.01)
    *C02F 1/72*    (2006.01)
    (Continued)

(52) U.S. Cl.
    CPC .... *C12Y 305/01005* (2013.01); *B01J 20/2805* (2013.01); *B01J 20/321* (2013.01);
    (Continued)

(58) Field of Classification Search
    CPC .................. C02F 1/725; C12Y 305/01005
    USPC ................ 210/754; 435/195, 227–231
    See application file for complete search history.

(56) References Cited

U.S. PATENT DOCUMENTS 4,793,935 A * 12/1988 Stillman ............... C02F 1/5236
                                                        210/727
6,673,582 B2 * 1/2004 McTavish ..................... 435/122
(Continued)

FOREIGN PATENT DOCUMENTS

| AU | 41971   | 5/1979 |
|----|---------|--------|
| GB | 2025919 | 1/1980 |

(Continued)

OTHER PUBLICATIONS

Examiner's Report Dated Oct. 6, 2010 From the Australian Government, IP Australia Re. Application No. 2007228391.
(Continued)

*Primary Examiner* — Peter Keyworth
(74) *Attorney, Agent, or Firm* — Browdy and Neimark, PLLC

(57) ABSTRACT

A composition-of-matter for use in water treatment, composed of a water-insoluble matrix and one or more amidohydrolase, such as cyanuric acid amidohydrolase, incorporated in or on the matrix, is disclosed. Also disclosed are devices containing same and methods utilizing same for water treatment. The water treatment is effected by an enzymatically-catalyzed reduction of the concentration of an amide-containing compound, such as cyanuric acid, found in chlorinated water of swimming polls, spas and other similar structures.

14 Claims, 11 Drawing Sheets
(7 of 11 Drawing Sheet(s) Filed in Color)

(51) Int. Cl.
| | |
|---|---|
| *C02F 3/34* | (2006.01) |
| *C12N 9/80* | (2006.01) |
| *C12N 9/86* | (2006.01) |
| *C12N 11/00* | (2006.01) |
| *B01J 20/32* | (2006.01) |
| *B01J 20/28* | (2006.01) |
| *C02F 101/34* | (2006.01) |
| *C02F 101/38* | (2006.01) |
| *C02F 103/42* | (2006.01) |
| *A61K 38/00* | (2006.01) |

(52) U.S. Cl.
CPC .......... *B01J20/3204* (2013.01); *B01J 20/3212* (2013.01); *B01J 20/3219* (2013.01); *B01J 20/3274* (2013.01); *C02F 1/725* (2013.01); *C02F 3/342* (2013.01); *C12N 9/80* (2013.01); *C12N 9/86* (2013.01); *C12N 11/00* (2013.01); *C12Y 305/01084* (2013.01); *C12Y 305/02015* (2013.01); *A61K 38/00* (2013.01); *C02F 2101/34* (2013.01); *C02F 2101/38* (2013.01); *C02F 2103/42* (2013.01); *C02F 2301/046* (2013.01); *C02F 2303/18* (2013.01)

(56) References Cited

U.S. PATENT DOCUMENTS

| | | | | |
|---|---|---|---|---|
| 7,238,287 | B2* | 7/2007 | Kulperger | 210/632 |
| 2002/0045236 | A1 | 4/2002 | Wackett et al. | |
| 2003/0098270 | A1* | 5/2003 | Thompson | 210/283 |
| 2006/0024808 | A1* | 2/2006 | Darzins et al. | 435/195 |
| 2006/0289344 | A1* | 12/2006 | Queirel | 210/167.1 |
| 2007/0095760 | A1* | 5/2007 | Girvan et al. | 210/696 |

FOREIGN PATENT DOCUMENTS

| | | |
|---|---|---|
| JP | 06-086997 | 3/1994 |
| RU | 1178079 | 4/1994 |
| WO | WO 2007/107981 | 9/2007 |

OTHER PUBLICATIONS

International Preliminary Report on Patentability Dated Dec. 11, 2008 From the International Bureau of WIPO Re.: Application No. PCT/IL2007/000336.
International Search Report and the Written Opinion Dated Jul. 8, 2008 From the International Searching Authority Re. Application No. PCT/IL07/00336.
Communication Pursuant to Rules 70(2) and 70a(2) EPC Dated Jan. 13, 2012 From the European Patent Office Re. Application No. 07713356.9.
Supplementary European Search Report and the European Search Opinion Dated Dec. 27, 2011 From the European Patent Office Re. Application No. 07713356.9.
Kaplun et al. Database WPI, Week 199507, XP002665268, AN 1995-049825.
Kawachi et al. Database WPI , Week 199417, XP002665267, AN 1994-140646.
Stamper et al. "Ring-Cleaving Cyanuric Acid Amidohydrolase Activity in the Atrazine-Mineralizing Ralstonia Basilensis M91-3", Database Compendex [Online], XP002665270, Database Accession No. E2006049659007, Nov. 2005. Abstract.
Wackett et al. "Biodegradable of Atrazine and Related S-Triazine Compounds: From Enzymes to Field Studies", Database BIOSIS [Online], XP0026665269, Database Accession No. PREV200200181423, Jan. 2002. Abstract.
Office Action Dated Oct. 28, 2014 From the Israel Patent Office Re. Application No. 194106 and Its Translation Into English.
Requisition by the Examiner Dated Feb. 12, 2015 From the Canadian Intellectual Property Office Re. Application No. 2,645,147.

* cited by examiner

SEQUENCE LISTING

<160> NUMBER OF SEQ ID NOS: 7

<210> SEQ ID NO 1
<211> LENGTH: 10
<212> TYPE: PRT
<213> ORGANISM: Artificial sequence
<220> FEATURE:
<223> OTHER INFORMATION: His tag

<400> SEQUENCE: 1

Leu Glu His His His His His His His His
1               5                   10

<210> SEQ ID NO 2
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 2
acgactcgag agctgtgcgc gcgataactg c                                    31

<210> SEQ ID NO 3
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 3
gtcacatatg caagcgcaag tttttcgagt tcc                                  33

<210> SEQ ID NO 4
<211> LENGTH: 27
<212> TYPE: DNA
<213> ORGANISM: Artificial sequence
<220> FEATURE:
<223> OTHER INFORMATION: A polynucleotide coding TRZD C'

<400> SEQUENCE: 4
cccgttgcag ttatcgcgcg cacagct                                         27

<210> SEQ ID NO 5
<211> LENGTH: 60
<212> TYPE: DNA
<213> ORGANISM: Artificial sequence
<220> FEATURE:
<223> OTHER INFORMATION: A polynucleotide coding TRZD C' fused to a His
      tag

<400> SEQUENCE: 5
cccgttgcag ttatcgcgcg cacagctctc gagcaccacc accaccacca ccaccactaa    60

<210> SEQ ID NO 6
<211> LENGTH: 9
<212> TYPE: PRT
<213> ORGANISM: Artificial sequence
<220> FEATURE:
<223> OTHER INFORMATION: TRZD C' polypeptide

<400> SEQUENCE: 6

Pro Val Ala Val Ile Ala Arg Thr Ala
1               5

<210> SEQ ID NO 7

```
<211> LENGTH: 19
<212> TYPE: PRT
<213> ORGANISM: Artificial sequence
<220> FEATURE:
<223> OTHER INFORMATION: TRZD C' polypeptide fused to a His tag

<400> SEQUENCE: 7

Pro Val Ala Val Ile Ala Arg Thr Ala Leu Glu His His His His
1               5                   10                  15

His His His
```

METHODS, COMPOSITIONS AND DEVICES FOR MAINTAINING CHEMICAL BALANCE OF CHLORINATED WATER

RELATED APPLICATIONS

This application is a National Phase Application of PCT Application No. PCT/IL2007/000336 having International Filing Date of Mar. 14, 2007, which claims the benefit of U.S. Provisional Patent Application No. 60/783,028, filed on Mar. 17, 2006. The contents of the above Applications are all incorporated herein by reference.

FIELD AND BACKGROUND OF THE INVENTION

The present invention relates to methods, compositions and devices for chemical balancing of chlorinated water, and more particularly, to methods compositions and devices of modulating the level of amide-containing chemicals such as cyanuric acid in chlorinated water of swimming pools, spas and similar water reservoirs.

Artificial swimming pools are known to have been built by the ancient Greeks and Romans who used them for athletic training in the palestras as well as for nautical games and military exercises. Roman emperors had private swimming pools in which fish also were kept, whence the Latin word for pool, piscina. In modern days, open air swimming pools represent a major worldwide attraction for children and adults all over the world as a recreational pastime, as providing the means for one of the most beneficial forms of exercise and as serving one of the major national and Olympic sports. The ever growing number of swimming pools is estimated to be in excess of 20 millions pools worldwide. Preserving the water quality of these pools is a major health and aesthetic concern and the source of an industry and business of several hundreds of millions of US dollars a year.

Maintaining the water quality in swimming pools, spas, hot-tubs, waterslides, and other circulating reservoirs for sports, recreational, therapeutic and ceremonial bathing, as well as decorative landscaping structures such as fountains and pools, presents a considerable challenge in which a critical balance has to be preserved between the various oxidizers, sanitizers, clarifiers, conditioners, disinfectants and the likes that are added to the pool or are formed therein. The life time in the pool water of most chemicals, is limited by their chemical and/or photochemical degradation, evaporation and/or removal by filtration, backwashing, drainage, spillage and sedimentation.

"Free chlorine", a phrase which is used herein to describe $Cl^+$, is a highly effective antimicrobial agent, which has a wide biocidal activity (e.g., antibacterial, antifungal, antialgal and antiviral activities). It is routinely used in water treatment systems. Hypochlorous acid, HOCl, is a common source of free chlorine, via the hypochlorite ion $OCl^-$ (see, scheme 1 below), and is typically used as an aggressive oxidizing and chlorinating agent for various applications, including water purification systems.

Scheme 1

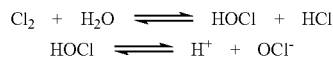

The mechanism of the biocidic action exerted by free chlorine-producing agents, such as sodium hypochlorite and hypochlorous acid, is not fully understood. It is assumed that free chlorine is responsible for the oxidation reactions with the cytoplasm of microorganisms (e.g., bacteria, vegetative bacteria, algae, spore, virus, or fungus), after diffusion through the cell walls. Hypochlorous acid penetrates the cell walls readily due to its size, structure and neutrality, which are similar to that of water. Once present in the cell, chlorine disturbs the production of ATP (adenosine triphosphate), an essential compound for the respiration of microorganisms, as well as the structure and thus activity of polynucleic acids, which are essential for all cell functions and reproduction.

Direct use of chlorine gas and/or HOCl is limited due to their high reactivity and aggressiveness as oxidizing agents. Hence, the use of compounds that are capable of releasing HOCl and thus act as indirect oxidizing agents is preferred.

Chemical compounds which release a halogen disinfectant agent when coming in contact with water, primarily free chlorine donor biocides, are the major and most commonly used sanitizers in swimming pools. These sanitizers ensure that the water in the swimming pool remains clean and safe for the swimmers throughout the day. However, hypochlorous acid is highly unstable, and readily decomposes into inactive breakdown products, such as hydrochloric acid, water and oxygen, via UV radiation driven photochemical reactions upon exposure to direct sun light, and/or upon exposure to moderate and high temperatures. During the summer, which is the peak season for swimming pools, up to 90% of the total active chlorine species are lost in a sunny day over two to three hours. In order to control these effects and preserve the effectiveness of the chlorine, agents aimed at stabilizing the chlorine are often added to the water.

The most commonly used and effective chlorine stabilizer is cyanuric acid, also known by its tautomer's name, s-triazinetrione or isocyanuric acid (see, Scheme 2 below).

Scheme 2

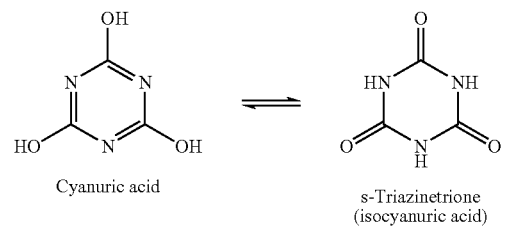

Cyanuric acid        s-Triazinetrione
                     (isocyanuric acid)

Cyanuric acid, as well as cyanurate salts and various derivatives thereof are compounds which protect the chlorine from the negative effects of UV and heat, and therefore practically reduce the amount of chlorine which needs to be added to the water in order to maintain safe conditions of disinfection. The protection action of these compounds is achieved by the ability of free chlorine, $Cl^+$, to reversibly bind to the nitrogen atoms in the cyanuric acid ring, as depicted in Scheme 3 below.

Scheme 3

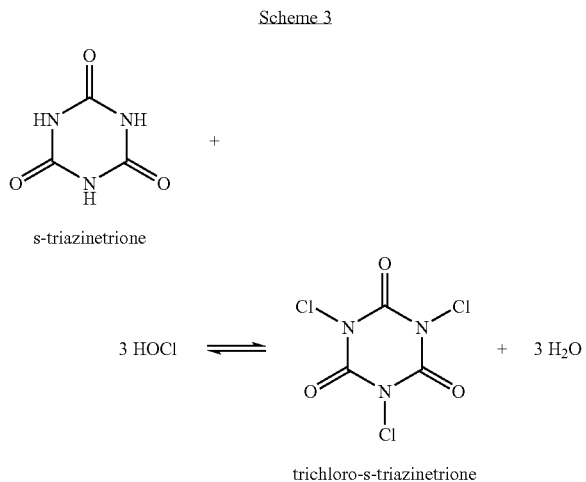

s-triazinetrione trichloro-s-triazinetrione

This relatively slow equilibrium keeps some of the hypochlorous acid in this bound form, thus protecting it from photochemical decomposition as long as the $Cl^+$ is bound to the triazine ring.

Hence, cyanuric acid, as well as cyanurate salts and various derivatives thereof, are commonly added to most commercially available chlorine tablets, or used as a separate chemical in addition to active-chlorine generating compounds.

With a correct dosing, cyanuric acid can reduce the chlorine consumption during the sunny season. Pool water treated with 25 to 50 milligrams per liter of cyanuric acid loses only 10 to 15 percent of their total chlorine as compared to untreated water under the same conditions. However, incorrect balance of cyanuric acid can create an over-protective effect and hence substantially decrease the effectiveness of chlorine as a disinfectant.

More common are sanitizing chemicals which are based on N-halogenated cyanurate compounds such as trichlorocyanuric acid (TCCA, trichloro-s-triazinetrione or 1,3,5-trichloro-[1,3,5]triazinane-2,4,6-trione; see, Scheme 3 above), halogenated hydantoins such as 1-bromo-3-chloro-5,5-dimethylhydantoin (BCDMH), 1,3-dichloro-5,5-dimethylhydantion (DCDMH), and 1,3-dichloro-5-ethyl-5-methylhydantoin, halogenated melamines such as N,N,N-trichloromelamine, and halogenated glycolurils such as N,N,N,N-tetrachloroglycoluril, salts thereof for faster dissolution in water, and combinations thereof. Such compounds have dual effect: release of active chlorine species and controlling the level of chlorine species in water.

Due to gradual and unavoidable degradation of hypochlorous acid in the water, routine addition of these commonly used stabilized chlorine-based sanitizers mentioned above, such as trichloroisocyanuric acid (trichloro-s-triazinetrione) or its faster dissolving sodium dichloroisocyanurate (sodium dichloro-s-triazinetrione), bring about a gradual rise in cyanuric acid concentration in the pool's water. An ideal cyanuric acid level, suitable for public swimming pools and spas, should be maintained at about 50 ppm (parts per million), with an acceptable range of 30 to 70 ppm. To achieve 50 ppm of cyanuric acid, 2 kilograms of the stabilizer must be added to 40 cubic meters ($m^3$) of chlorinated pool water.

Excessive amounts of cyanuric acid drive the equilibrium, depicted in Scheme 3 above, towards the uptake of free chlorine. Hence, excessive amounts of cyanuric acid cause the chlorine to become progressively over-stabilized and interfere with its disinfection function. The phenomenon known as "chlorine-lock" takes place when the concentration of cyanuric acid reaches over 100 ppm (0.77 mM). Chlorine-lock expresses itself similarly to inadequately low chlorine level, in clouding of the pool's water which, apart from an aesthetic nuisance, is a clear indication that the water is no longer safe for use.

Once added to the pool, cyanuric acid does not dissipate or degrade substantially. It is removed from the pool only by splash-out and backwash waste procedures or dilution. Typically, cyanuric acid level is lowered by draining part of the pool's water and diluting the remaining water with fresh water. If the cyanuric acid level exceeds 100 ppm considerably, the pool ought to be partially or totally drained and have its inner-walls scrubbed (cyanuric acid will sediment on the sides of the pool). This time-consuming and water-wasteful process is extremely costly not only in terms of water but also in lost of pool's operational time, additional stabilized chlorine added, and the so far unavoidable reiterative nature of the overall process needed to maintain the balance between the concentration of reactive chlorine species and the concentration of cyanuric acid.

Reservoir water, including water of swimming pools and spas, is typically treated in closed or semi-closed systems which circulate the water through a water treatment plant comprising filters and other devices for monitoring and adjusting the chemical balance of the water.

Filters of various mesh size remove particulates from the water without changing the chemical composition of the water in terms of dissolved chemicals. Other devices such as ion exchange columns, typically used to adjust the pH of the water and to remove salts and other dissolved chemicals, and erosion chemical feed systems, also known as erosion feeders which are typically used to gradually add chemicals to the water, are responsible for adjusting the chemical composition of the water.

Water filtration, treatment and purification devices are disclosed for example, in U.S. Pat. Nos. 3,957,617, 4,412,919, 4,969,996, 5,108,606, 5,336,398, 5,688,588, 6,627,073, 6,649,045, 6,887,379 and 6,932,889. The main concept of these water treatment devices is passing pre-treated water through a device which comprises a container filled with an insoluble solid granulose matrix. This matrix, once packed in the container, remains penetrable to water by virtue of channels and interconnected cavities in and between the matrix granules, having a predetermined maximal mesh size, which effects the filtration, purification and treatment of the water by absorbing or otherwise eliminating undesired substances in the water entering the device, and in some cases adding desired substances to the water exiting the device.

Other methods for treatment of water include physico-chemical means such as irradiation with biocidic radiation such as UV or gamma, heating, distillation, subjection to magnetic and/or electric fields, vortices and centrifugation, and the likes.

Recently, a new approach for chemical adjustment of pool water has employed biochemical catalysts, namely enzymes. U.S. Pat. No. 6,372,472 teaches filter media containing powdered cellulose and immobilized lipase for swimming pool and spa water filtration and treatment. This filtering media absorbs oils contained in pool or spa water, and the lipase hydrolyzes the oils, thus ridding the water of a major and common esthetic nuisance.

Immobilization of proteins, including enzymes, while retaining the biochemical activity thereof, on solid support of various materials, is disclosed in numerous publications such as U.S. Pat. Nos. 4,071,409, 4,090,919, 4,258,133, 4,888,285, 5,177,013, 5,998,183, 6,905,733, and 6,987,079, U.S.

Patent Application No. 2003/0096383, and other publications such as Yan A-X. et al., 2002, *Applied Biochemistry and Biotechnology*, Vol. 101(2), pp. 113-130(18); and Ye, Yunhua et al., 2004, *Peptide Science*, Vol. 41, pp 613-616.

None of these methods and devices, however, effects the removal or otherwise lowering cyanuric acid levels in water reservoirs, such as pools or spas. As discussed hereinabove, to date, removal of cyanuric acid involves time and cost consuming actions such as draining the water reservoir.

There is thus a widely recognized need for, and it would be highly advantageous to have methods and devices which can modulate the levels of cyanuric acid in water, devoid of the above limitations.

SUMMARY OF THE INVENTION

According to one aspect of the present invention there is provided a composition-of-matter comprising a water-insoluble matrix and at least one amidohydrolase incorporated in or on the matrix, the composition-of-matter being identified for use in water treatment.

According to further features in preferred embodiments of the invention described below, the water treatment comprises reducing a concentration of at least one amide-containing compound in water.

According to another aspect of the present invention there is provided a device for water treatment comprising at least one casing having the composition-of-matter of claim 1 embedded therein such that water flowing through the casing becomes in contact with the composition-of-matter.

According to further features in preferred embodiments of the invention described below, the water treatment is effected by reducing a concentration of at least one amide-containing compound in the water.

According to still further features in the described preferred embodiments the casing comprises a filter cartridge having at least two parallel perforated faces.

According to still another aspect of the present invention there is provided a method of treating water comprising contacting water with the device described herein.

According to further features in preferred embodiments of the invention described below, the contacting comprises passing the water through the device.

According to still further features in the described preferred embodiments the water treatment comprises reducing a concentration of at least one amide-containing compound in the water.

According to still further features in the described preferred embodiments the water treatment is effected during a time period of 20 hours or less.

According to still further features in the described preferred embodiments passing the water through the device is effected at a flow rate of at least 10 cubic meters per hour.

According to still further features in the described preferred embodiments the water comprises chlorinated water used in a circulating water reservoir.

According to still further features in the described preferred embodiments the circulating reservoir is selected from the group consisting of a pool, a swimming pool, a spa, a hot-tub, a whirlpool bath, a fountain and a waterslide.

According to still further features in the described preferred embodiments the amidohydrolase is selected from the group consisting of cyanuric acid amidohydrolase, biuret amidohydrolase, urease and any combination thereof.

According to still further features in the described preferred embodiments the amidohydrolase is cyanuric acid amidohydrolase and the amide-containing compound is cyanuric acid.

According to still further features in the described preferred embodiments the concentration of the cyanuric acid in the water, subsequent to the reducing, is less than 100 ppm.

According to still further features in the described preferred embodiments the concentration of the cyanuric acid in the water, subsequent to the reducing, ranges from 70 ppm to 30 ppm.

According to still further features in the described preferred embodiments an amount of the cyanuric acid amidohydrolase is at least 2.5 mg per one cubic meter of the water.

According to still further features in the described preferred embodiments the water-insoluble matrix is granular and/or porous.

According to still further features in the described preferred embodiments the water-insoluble matrix is selected from the group consisting of an organic matrix and an inorganic matrix.

According to still further features in the described preferred embodiments the organic matrix is selected from the group consisting of plastic, nylon, activated carbon, cellulose, agarose, chitin, chitosan, collagen and polystyrene.

According to still further features in the described preferred embodiments the inorganic matrix is selected from the group consisting of glass, zeolite, silica, alumina, titania, zirconia, calcium alginate and celite.

The present invention successfully addresses the shortcomings of the presently known configurations by providing novel compositions-of-matter which can be efficiently utilized for chemical balancing chlorinated water, and particularly for reducing the concentration of cyanuric acid in chlorinated water reservoirs, while circumventing the need to drain the water reservoir, and which further overcome the limitations associated with the presently known techniques in this field.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
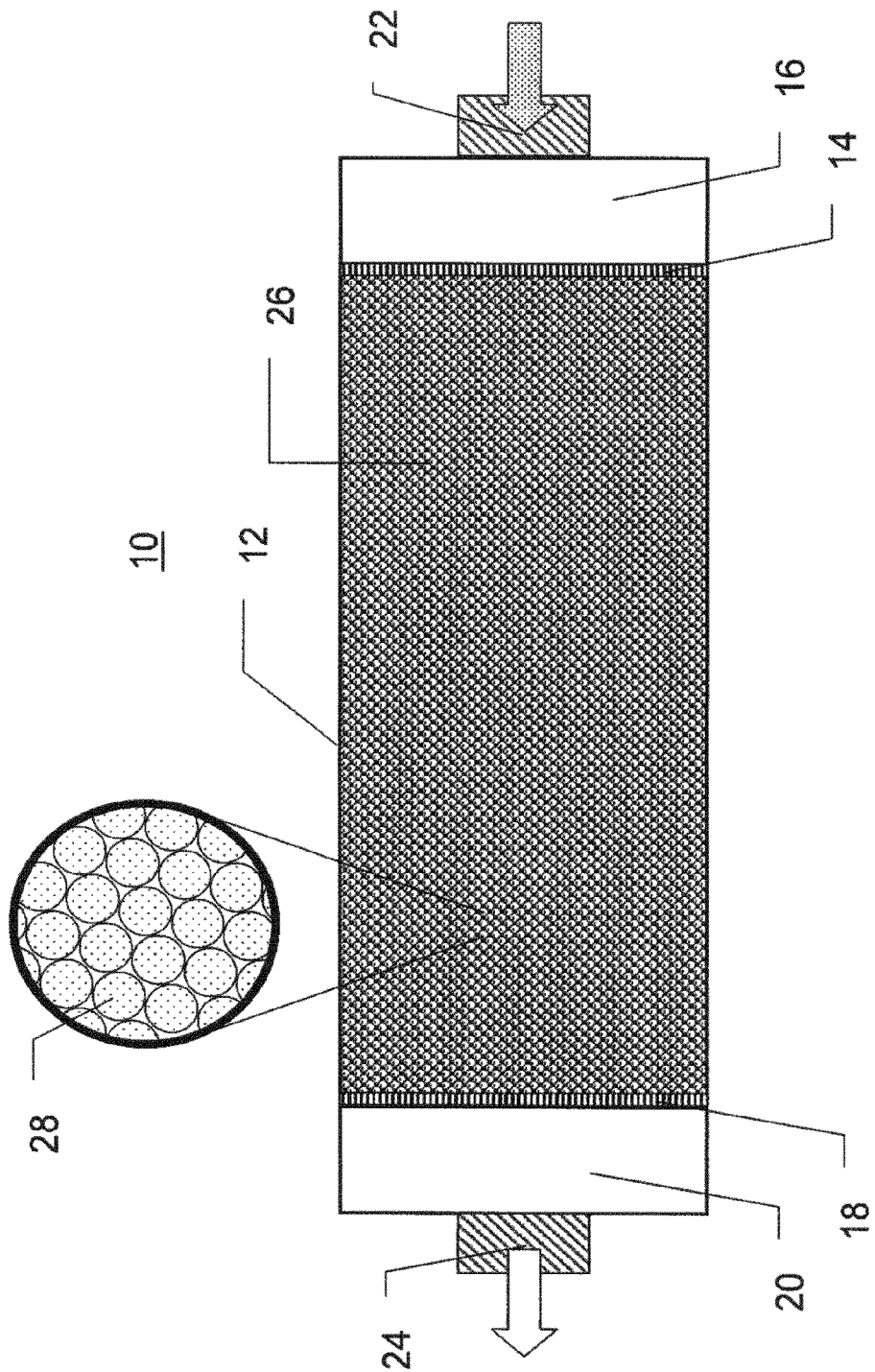
Figure 2:
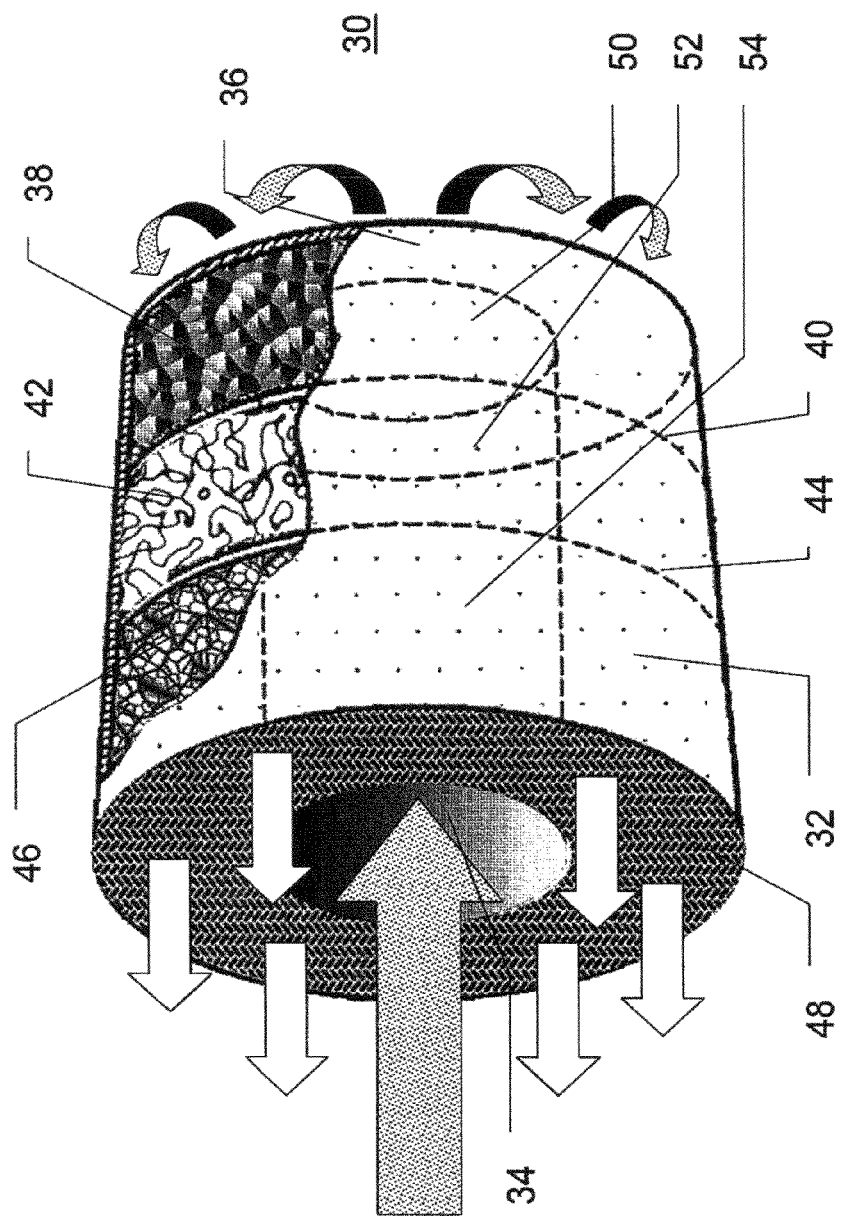
Figure 3:
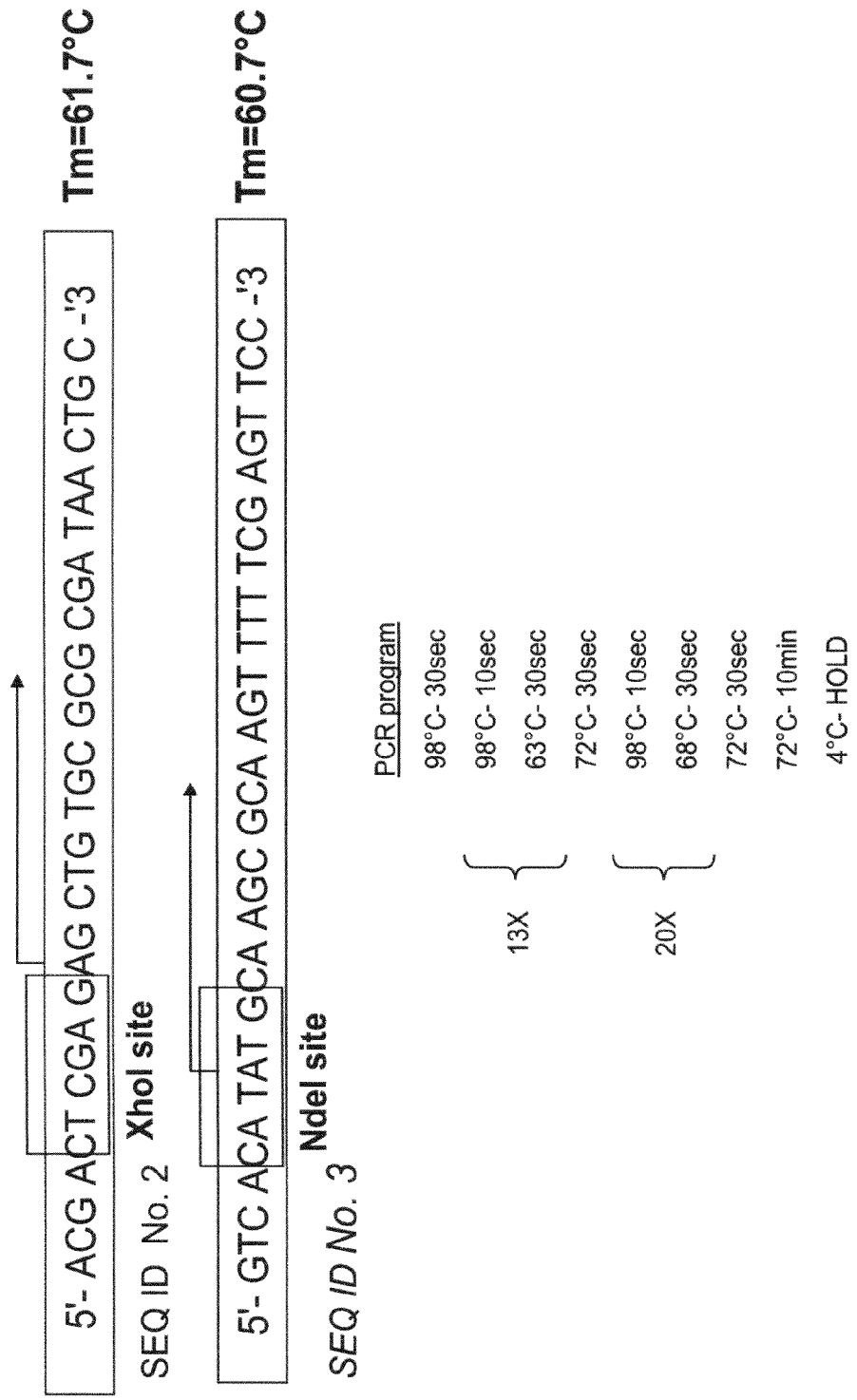
Figure 4:
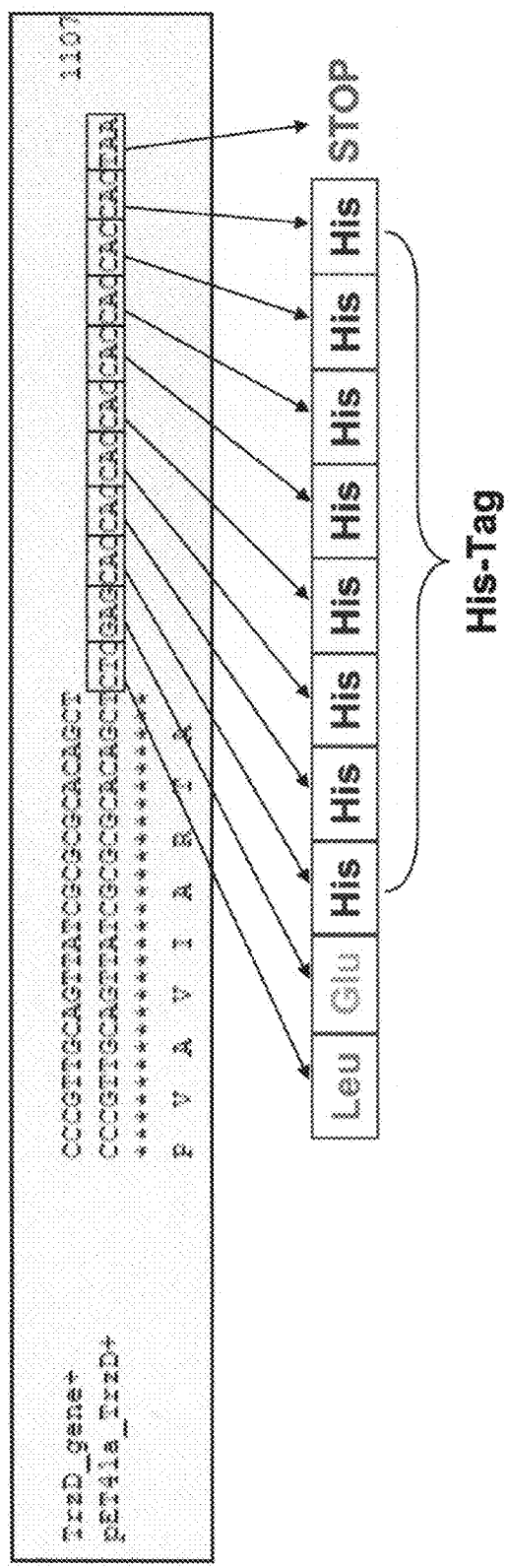
Figure 5:
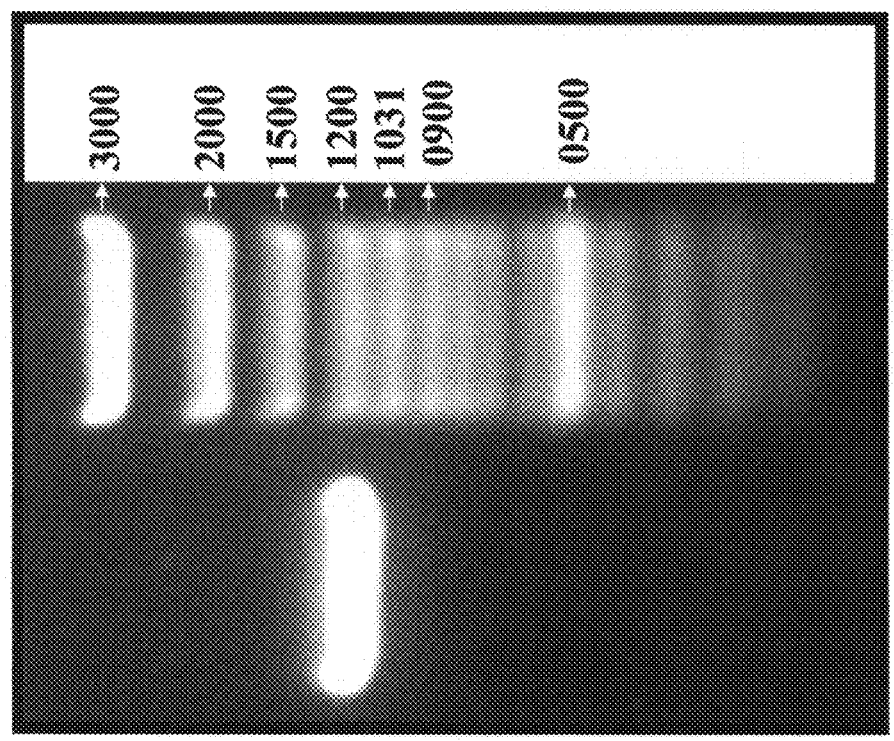
Figure 6:
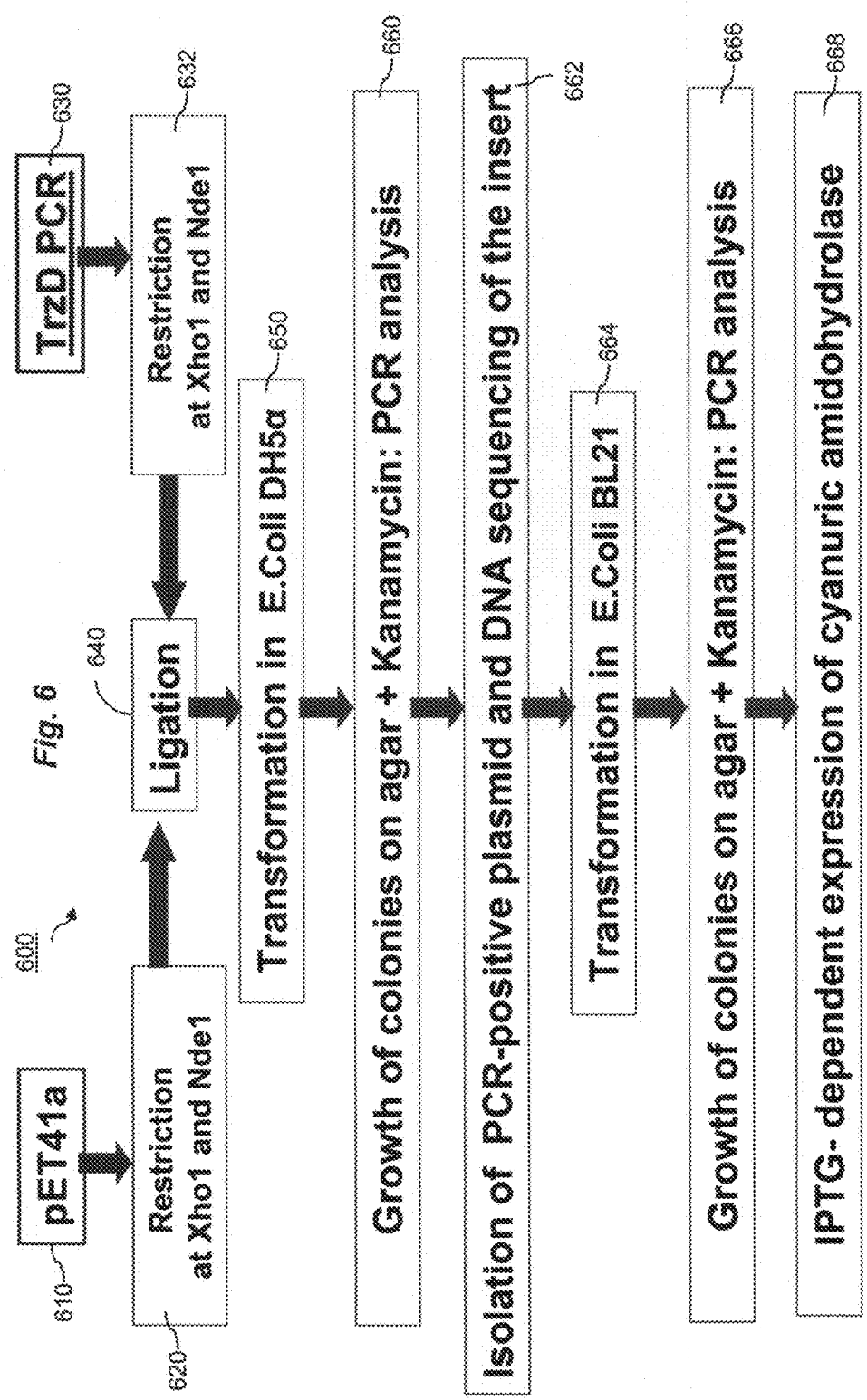
Figure 7:
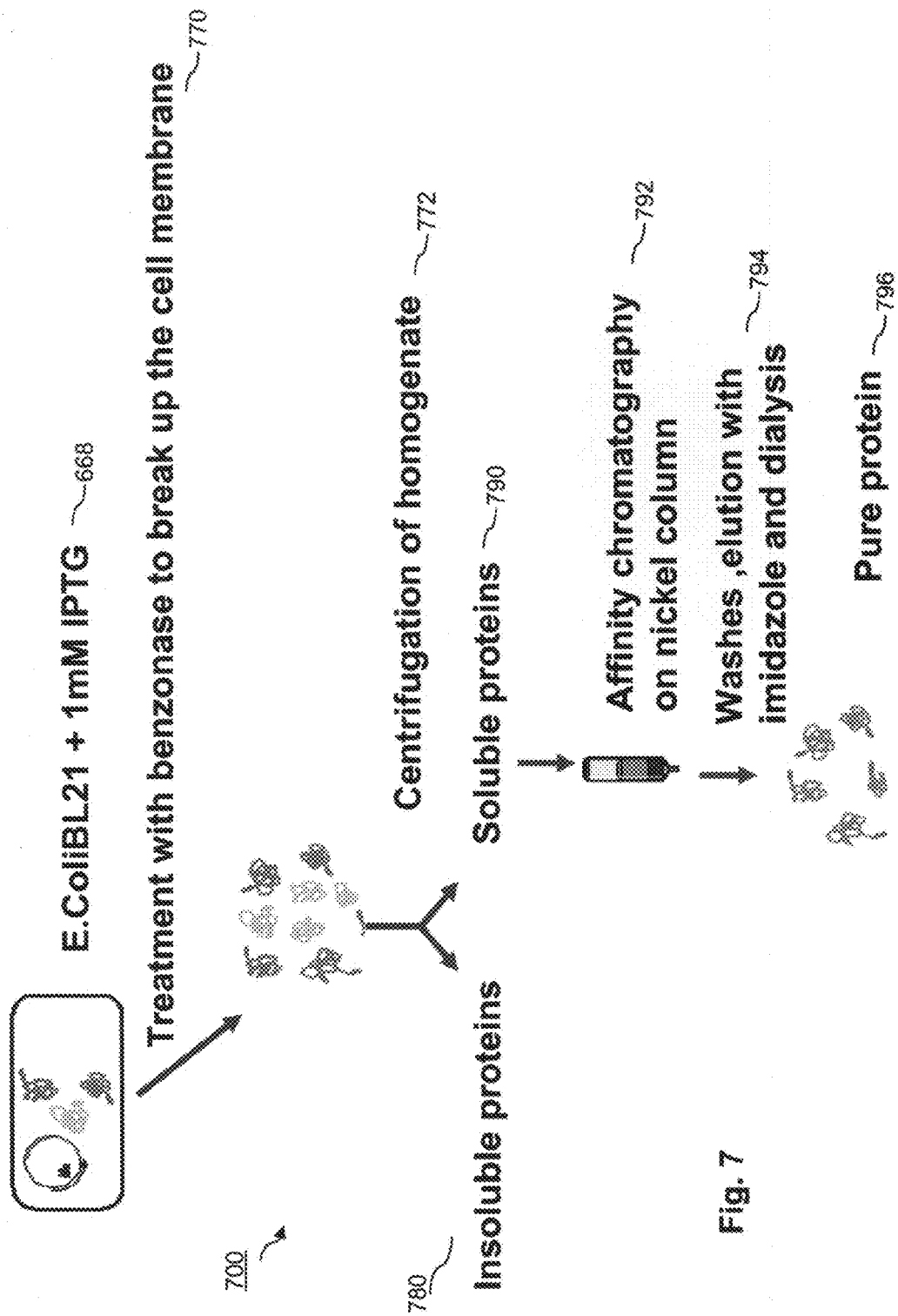
Figure 8:
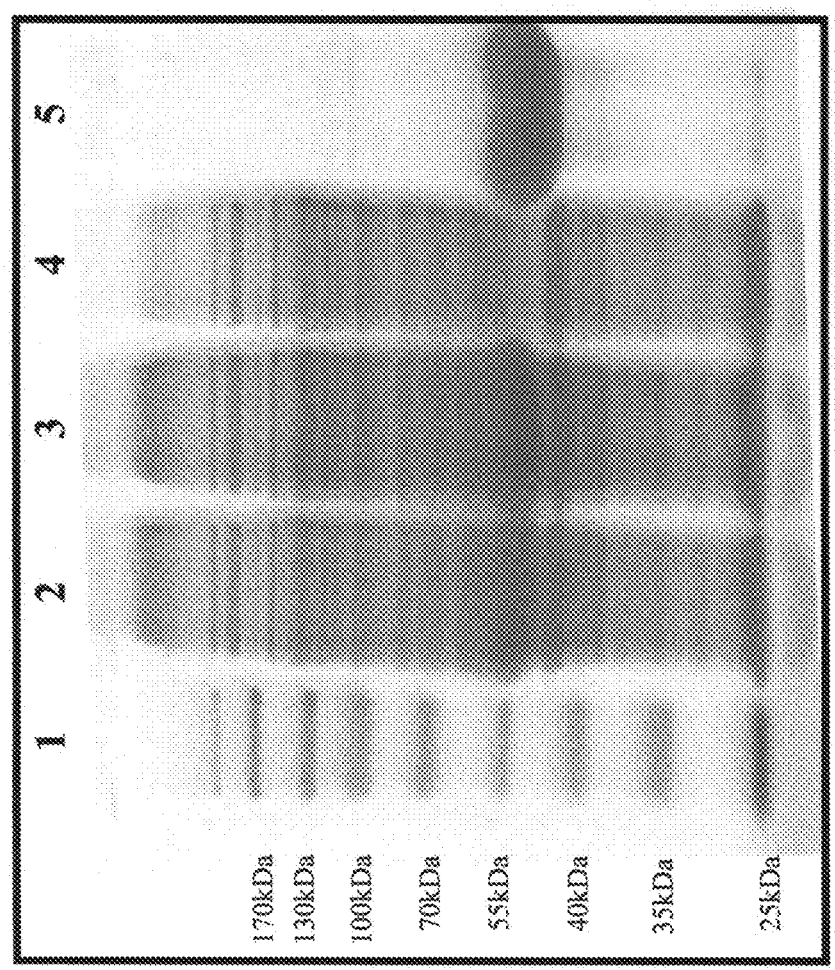
Figure 9:
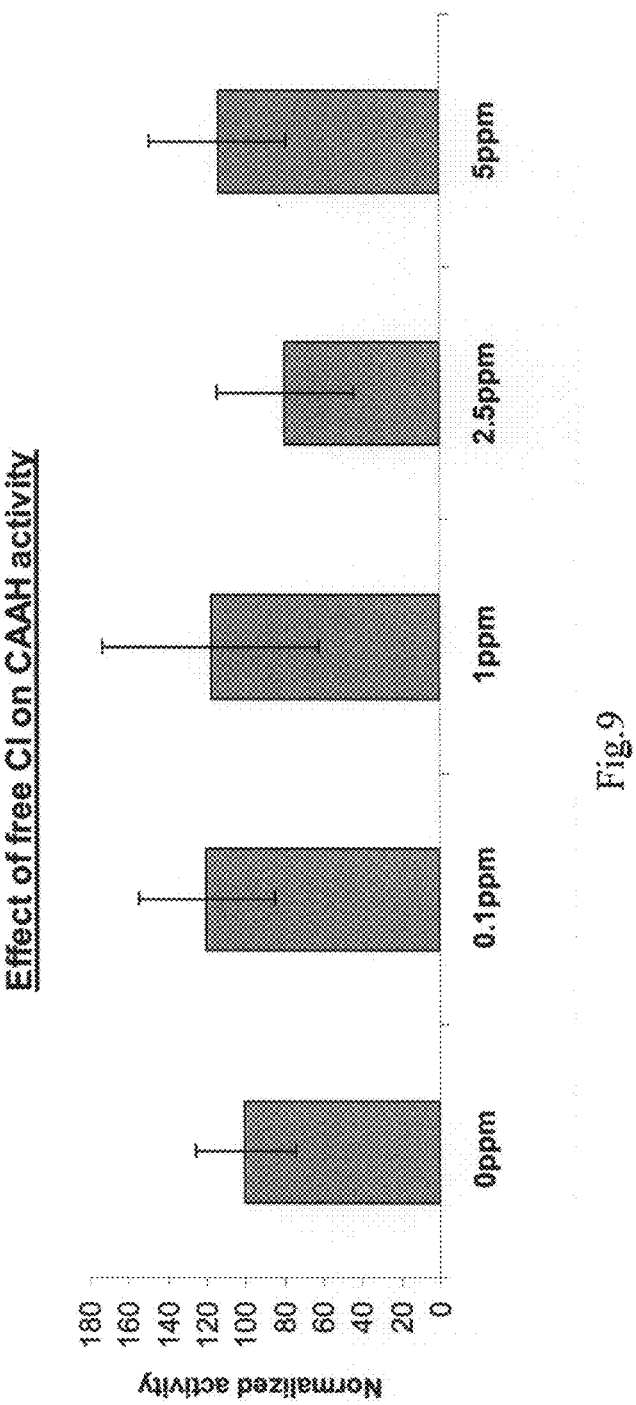
Figure 10:
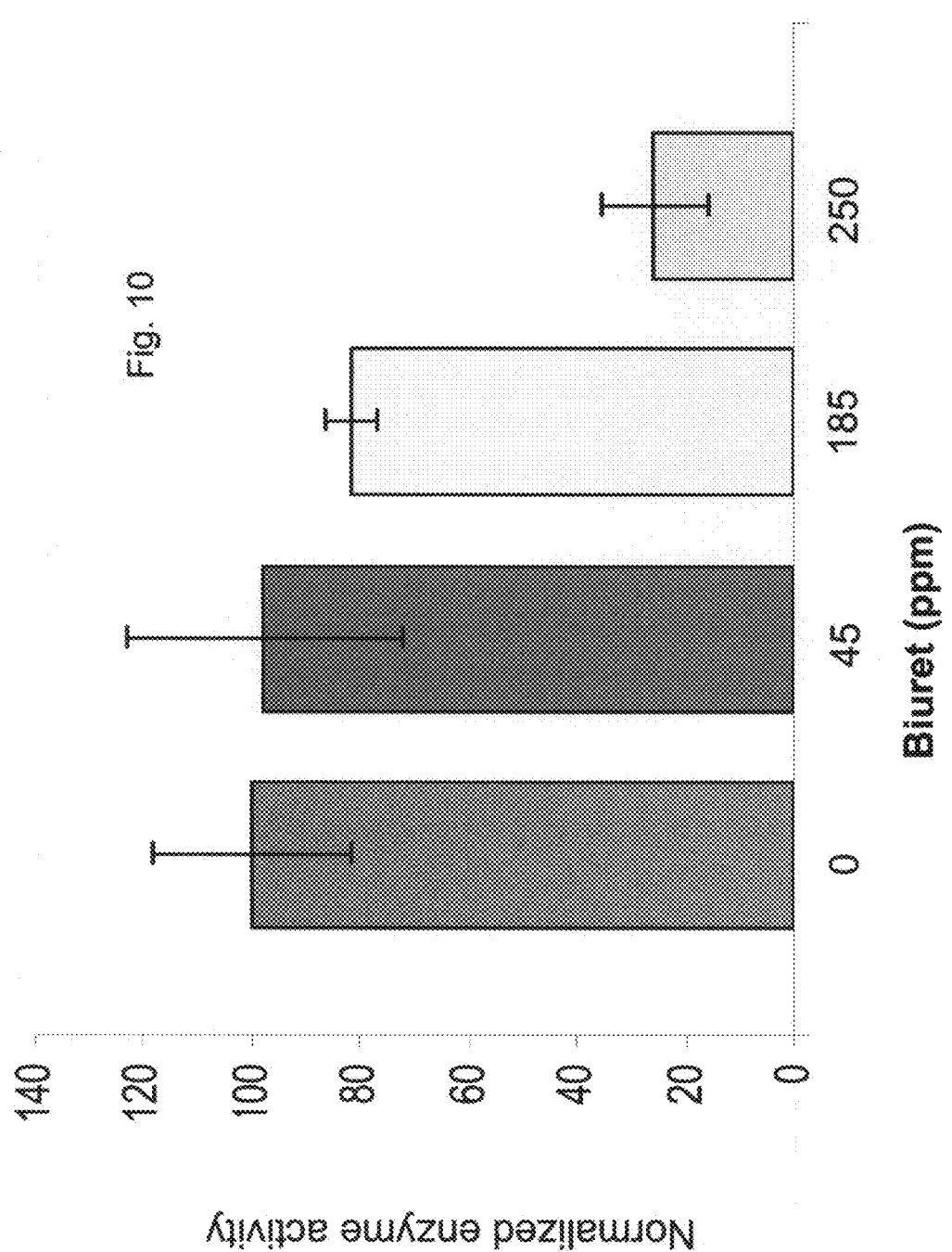
Figure 11:
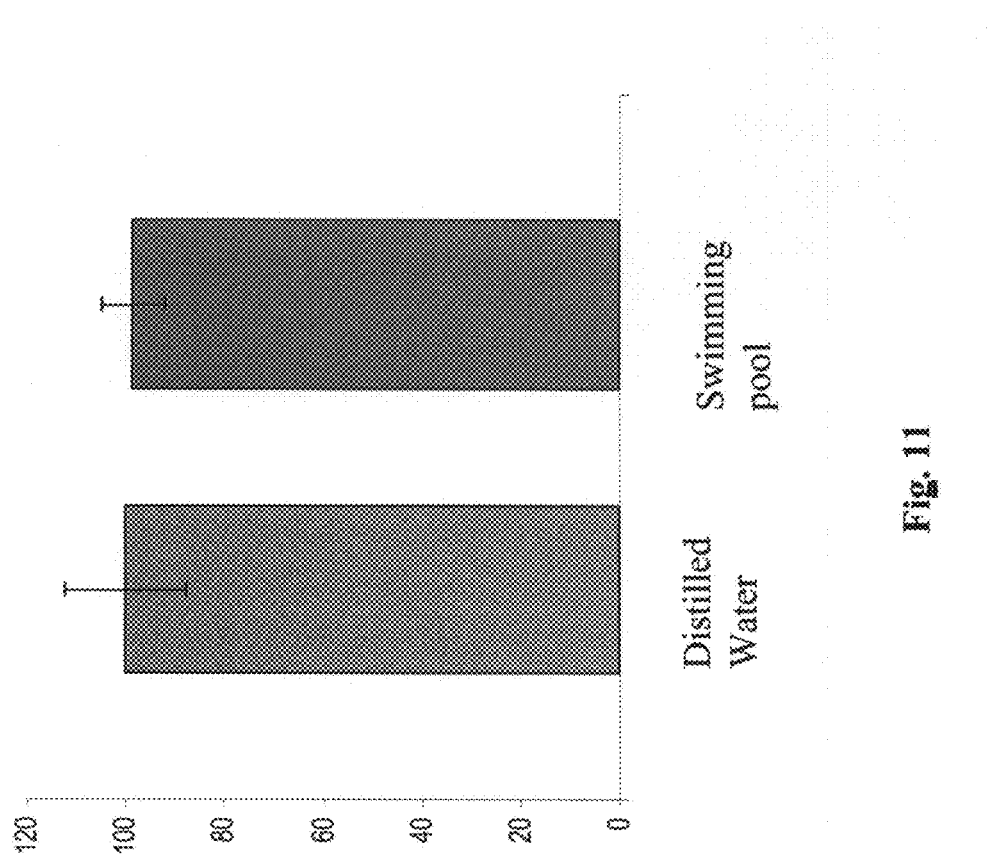

FIG. 1 presents a simplified illustration of a typical water-treatment column, representing an exemplary device for water treatment according to the present invention, designed to lower the concentration of cyanuric acid in water, which is composed of a pressure-resistant casing bounded by an upstream and a downstream perforated faces through which untreated water flow and come in contact with a composition-of-matter, comprised of water-permeable and water-insoluble matrix and cyanuric acid amidohydrolase, embedded in the casing;

FIG. 2 presents a simplified illustration of a triple-action water-treatment cartridge, representing an exemplary device for water treatment according to the present invention, designed to effect total degradation of cyanuric acid in water to $CO_2$ and ammonia, which is composed of three sub-compartments separated by perforated faces, each having a different composition-of-matter comprising an enzyme for each degradation step of cyanuric acid;

FIG. 3 depicts graphically PCR primers identified as SEQ ID Nos. 2 and 3 with relevant restriction enzyme sites;

FIG. 4 depicts graphically the C terminus of TrzD and addition of a his tag thereto at both nucleic acid and amino acid levels;

FIG. 5 depicts an ethidium bromide stained agarose gel of a PCR product comprising the TrzD sequence;

FIG. 6 is a simplified flow diagram illustrating an exemplary cloning and transformation of a TrzD-his gene followed by expression of the his-tagged enzyme in bacteria;

FIG. 7 is a simplified flow diagram illustrating an exemplary purification strategy for a TrzD-his enzyme expressed in bacteria;

FIG. 8 is a Coomassie stained SDS polyacrylamide gel depicting electrophoretic separation of samples from representative stages of a purification strategy according to FIG. 7;

FIG. 9 is a bar graph depicting TrzD-his enzyme activity as a function of free chlorine (ammonia) concentration;

FIG. 10 is a bar graph depicting TrzD-his enzyme activity as a function of biuret concentration; and FIG. 11 is a bar graph illustrating a lack of effect of simulated swimming pool conditions on TrzD-his enzyme activity.

DESCRIPTION OF THE PREFERRED EMBODIMENTS

The present invention relates to compositions containing an amidohydrolase incorporated in or on a water-insoluble matrix, which can be used for treating water and, more particularly, for maintaining a chemical balance in chlorinated water of e.g., swimming pools, spas and similar structures, in terms of reducing the level of amide-containing compounds such as cyanuric acid in the water.

The principles and operation of the compositions, methods and devices of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, water of closed circulating reservoirs, such as those serving for human bathing or otherwise come in contact with humans, must be treated constantly so as to keep it clean, safe and aesthetic. This treatment includes sanitizing the water against microbial growth, which is commonly effected by using active halogen-producing chemicals.

The most commonly used halogen-producing chemical generates hypochlorous acid (HOCl) upon contacting water. The use of HOCl as the active biocide, however, is limited by its sensitivity to heat and UV radiation, which results in a relatively fast degradation thereof into inactive species when exposed to ambient environmental conditions. These degrading conditions are heightened still in the summer, when swimming pools and other similar open water reservoirs experience the highest seasonal bather load, that is, when sanitizing treatment is most required.

In order to slow the degradation process of HOCl, pool operators use cyanuric acid as a stabilizer of HOCl. Nevertheless, while the addition of cyanuric acid slows the degradation process, HOCl still degrades and must be replenished continuously throughout the pool's operational period. Since most commonly used HOCl-generating chemicals comprise cyanuric acid and/or derivatives thereof in one form or another, the level of the stabilizer keeps rising with each cycle of replenishment of the sanitizer until the sanitizer is no longer effective as a result of over-stabilization. This state, which is known as "chlorine-lock", takes place when the concentration of cyanuric acid, which is a rather stable and persistent compound, reaches over 100 ppm (parts per million, corresponding to a 0.77 mM concentration), and its presence signifies that the water is no longer safe for its original use.

At present, removal of cyanuric acid from the water is achieved by draining the pool, which is water-, chemical- and time-consuming and hence is a costly, ineffective and environmentally hazardous process.

One way to overcome the disadvantageous present procedures of removing cyanuric acid is by a chemical process in which degradation of the cyanuric acid in water into benign break-down products thereof at mild conditions would be effected, so as to achieve a balanced concentration of cyanuric acid in the water. Such a process should be designed suitable for use in typical water treatment plants used in closed and semi-closed circulating water reservoirs such as found in public and private swimming pools and spas, sports facilities, amusement and recreational water-parks, outdoors and indoors fountains, pools and artificial ponds and the likes.

In a search for such a process, the present inventor has envisioned that enzymes which use cyanuric acid as a substrate can be efficiently utilized to achieve the desired goal. More particularly, it was conceived that an immobilized enzyme, which uses cyanuric acid as a substrate, incorporated in or on a water-insoluble matrix, could be efficiently utilized to effect the desired chemical decomposition of cyanuric acid. It was further conceived that by utilizing an immobilizing matrix which has a permeable layer, such enzyme-containing matrix could serve as a stationary phase for the reservoir's chlorinated water, while acting in an analogy to, e.g., ion-exchange chromatography.

Hence, according to one aspect of the present invention, there is provided a composition-of-matter which comprises a water-insoluble matrix and one or more enzymes from the amidohydrolase family incorporated in or on this matrix, the composition-of-matter being identified for use in water treatment.

As discussed hereinabove, water treatment in general, and treatment of water used in circulating reservoirs in particular, involves a complex set of procedures and processes, which are aimed at achieving a balance of the various chemicals in the water. Hence, the composition-of-matter presented herein is designed capable of treating water, such as chlorinated water of circulating reservoirs, as these are defined herein, by reducing the concentration of one or more amide-containing compounds, as defined herein, in the water.

The phrase "circulating reservoir", as used herein, refers to a structure for holding a relatively large amount of water. The relatively large amount of water means that the water is not replaced after every use, or rarely replaced in general for a long period of time in terms of months and hence maintaining the water is typically effected by a circulating procedure. In order to maintain the water, it at least partially pumped or otherwise transferred out of the structure and then back into the reservoir by means of a water transferring device such as, for example, a pump, while being passed via a water treatment plant. Typical, presently used, water treatment plants include water treatment devices, such as, for example, sensors, detectors, heaters, coolers, chemical feeders, chemical exchangers and filters of various purposes and designs.

Preferably the circulating reservoirs according to the present invention are public and/or private reservoirs which are used by humans for hygiene, sports, professional training, recreation, amusement, therapeutic and general bathing and for ceremonial and aesthetic purposes, and include, without limitation, pools, artificial ponds and lakes, swimming pools, spas, hot-tubs, whirlpool baths, fountains and waterslides.

Since the most frequently used water sanitizing chemicals are HOCl generating compounds, and since the most frequently used HOCl-stabilizing compound is cyanuric acid, the adverse chemical imbalance is circulating water reservoirs commonly requires chemical transformation and/or degradation of cyanuric acid and/or other amide-containing compounds that are derived from or related to cyanuric acid. Thus, the water treatment, according to the present embodiments, comprises enzymatically-catalyzed transformation of cyanuric acid, as well as other amide-containing compounds which are found in the water, so as to reduce the concentration of these compounds. This enzymatically-catalyzed transformation is effected by an amidohydrolase.

The term "amidohydrolase", as used herein, refers to an enzyme that catalyzes the hydrolysis of a C—N bond in an amide group. The amide groups serving as the substrates of amidohydrolases are not necessarily part of a peptide bond. Such enzymes are also referred to in the art as "deamidases" and "deamidizing enzymes", and typically belong to the family of enzymes having an EC number starting with 3.5.1.- and 3.5.2.-, as these are defined hereinbelow.

The phrases "EC number" or "Enzyme Commission numbers" refer to a numerical classification scheme for enzymes compiled by the Nomenclature Committee of the International Union of Biochemistry and Molecular Biology (NC-IUBMB), in consultation with the IUPAC-IUBMB Joint Commission on Biochemical Nomenclature (JCBN). This scheme is based on the chemical reactions the enzymes catalyze. As a system of enzyme nomenclature, every EC number is associated with a recommended name for the respective enzyme. According to this nomenclature, every enzyme code consists of the letters "EC" followed by four numbers separated by periods. These numbers represent a progressively finer classification of the enzyme. For example, the enzyme cyanuric acid amidohydrolase has the code EC 3.5.2.15 which is constructed as follows: 3 stands for hydrolases (enzymes that use water to break up some other molecule), 3.5 for hydrolases that act on carbon-nitrogen bonds, other than peptide bonds, 3.5.2 for those that act on carbon-nitrogen bonds in cyclic amides, and 3.5.2.15 for those that act on the carbon-nitrogen bond in the cyclic amide in cyanuric acid.

The relationship between the amidohydrolase and the amide-containing compound is the relationship between an enzyme and a compatible substrate thereof. Therefore the reduction of the concentration of an amide-containing compound is effected by the enzymatic degradation thereof.

Preferably, the amidohydrolase utilized in the various aspects of the present invention is one or more of cyanuric acid amidohydrolase (EC 3.5.2.15), biuret amidohydrolase (EC 3.5.1.84), and urease (EC 3.5.1.5).

These three enzymes, when utilized in a sequential process, are capable of totally degrading cyanuric acid totally into two gases, $CO_2$ and $NH_3$. The first step in the total degradation of cyanuric acid is catalyzed by cyanuric acid amidohydrolase in the hydrolysis reaction of cyanuric acid to biuret and $CO_2$. The second step in the total degradation of cyanuric acid is catalyzed by biuret amidohydrolase in the hydrolysis reaction of biuret to urea, $CO_2$ and $NH_3$. The final step in the total degradation of cyanuric acid is catalyzed by urease in the hydrolysis reaction of urea to $CO_2$ and two molecules of $NH_3$. The total degradation of cyanuric acid is depicted in Scheme 4 below.

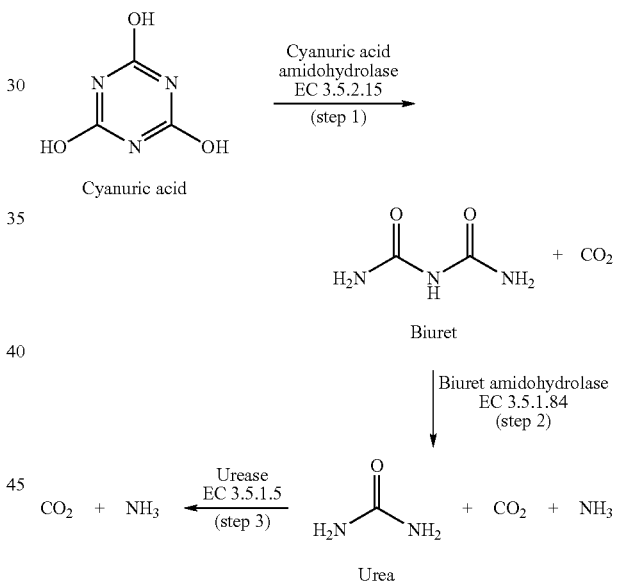

Since the first step in the total degradation of cyanuric acid is sufficient to alleviate the problem of chlorine-lock in chlorinated water discussed hereinabove, in a preferred embodiment, the amidohydrolase is a cyanuric acid amidohydrolase, and the amide-containing compound is cyanuric acid.

In other preferred embodiments, the cyanuric acid amidohydrolase is utilized in combination with one or more of the biuret amidohydrolase and urease described hereinabove.

Cyanuric acid amidohydrolase enzymes are well known in the art and have been isolated from various sources, some of which were characterized by their amino acid sequence, $K_M$ (Michaelis constant), Vmax, inhibitors thereof and other biochemical parameters. Sources of cyanuric acid amidohydrolase include man-made biological sources such as native and/or genetically engineered species including, for example, *Pseudomonas* sp, *Bradyrhizobium japonicum*, *Enterobacter cloacae*, *Hormodendrum* sp, *Klebsiella pneumoniae*, Moorella thermoacetica, Nocardioides sp, Penicillium sp and Rhodococcus corallinus, or any other source of the enzyme such as genetically modified microorganisms, plants and animals, which produce or over-produce the enzyme.

For example, the cyanuric acid amidohydrolase which was isolated from strain NRRLB-12227 of Pseudomonas sp., hydrolyses cyanuric acid to biuret and $CO_2$ with a $K_M$ of 0.05 mM, Vmax of 109.5 µmoles/min/mg at a turnover rate of 250 reactions per second and has an optimal catalytic pH of 8 at a temperature of 45° C. The cyanuric acid amidohydrolase from strain ADP of Pseudomonas sp. hydrolyses cyanuric acid with a $K_M$ of 0.071 mM, Vmax of 8.4 µmoles/min/mg at a turnover rate of 3 reactions per second.

Michaelis constant represents the dissociation constant (affinity for substrate) of the enzyme-substrate complex. Low values indicate that this complex is held together very tightly and rarely dissociates without the substrate first reacting to form the product.

In order that an enzyme would be used effectively for treating water in large volumes and rate, the enzyme needs to be an efficient catalyst; hence the biometric parameters of cyanuric acid amidohydrolase are of significance in the context of the present invention. The catalysis parameters of cyanuric acid amidohydrolase, namely $K_M$ values of 0.05 mM and 0.07 mM as presented hereinabove, signify that these enzymes can be used effectively to reduce the concentration of cyanuric acid in the water, so as to achieve a concentration lower than the chlorine-lock concentration of 100 ppm (corresponding to 0.77 mM). Even at the highest allowable concentration of cyanuric acid in such water, 0.62 mM, the enzyme is highly effective and can produce the desired hydrolysis.

The phrase "amide-containing compound", as used herein, refers to a compound which contains one or more amide group(s), as defined hereinbelow, and which is found in the water to be treated. The treatment, according to aspects of the present invention, comprises removal of this amide-containing compound by enzymatically catalyzing its decomposition to benign break-down products.

As used herein, the term "amide" refers to a R'—C(=O)—NR"R'" group, where R', R" and R'" are each hydrogen, amine, amide, alkyl, alkenyl, cycloalkyl, aryl, heteroaryl (bonded through a ring carbon) or heteroalicyclic (bonded through a ring carbon) as defined hereinbelow, or R' and one of R" and R'" may be connected so as to form a heteroaryl or heteroalicyclic ring.

As used herein, the term "amine" refers to an —NR'R" group where R' and R" are as defined herein.

The term "alkyl" as used herein, describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms.

The term "alkenyl" refers to an alkyl group which consists of at least two carbon atoms and at least one carbon-carbon double bond.

The term "cycloalkyl" describes an all-carbon monocyclic or fused ring (i.e., rings which share an adjacent pair of carbon atoms) group where one or more of the rings does not have a completely conjugated pi-electron system.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system.

The term "aryl" describes an all-carbon monocyclic or fused-ring polycyclic (i.e., rings which share adjacent pairs of carbon atoms) groups having a completely conjugated pi-electron system.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include triazine, pyrrole, furane, thiophene, imidazole, oxazole, thiazole, pyrazole, pyridine, pyrimidine, quinoline, isoquinoline and purine.

Examples, without limitation, of amide-containing compounds, which can be affected by the composition-of-matter presented herein, include cyanuric acid, biuret and urea, as these compounds are depicted in Scheme 4 hereinabove.

Other amide-containing compounds that can be present in the water of circulating reservoirs, stemming from designated chemical additives, natural organic fall-out (plant and insect material), human secretions and byproduct thereof, are also encompassed under the phrase "amide-containing compounds", and one or more enzymes can be selected so as to effect the enzymatically catalyzed degradation of each or a group of these amide-containing compounds.

Derivatives of cyanuric acid, biuret and urea, which may also be affected by the composition-of-matter presented herein, include salts thereof, and compounds which can degrade to cyanuric acid, biuret and urea in the water, either by spontaneous processes, photochemical processes and as a result of other chemical processes, or by an enzymatic reaction catalyzed by a corresponding enzyme.

For example, N-isopropylammelide, which can serve as a stabilizer for HOCl, as discussed hereinabove, can be degraded in water by N-isopropylammelide isopropylaminohydrolase (EC 3.5.99.4) to cyanuric acid and isopropylamine (see, Scheme 5 below). The product, cyanuric acid, may then be degraded by cyanuric acid amidohydrolase as discussed herein.

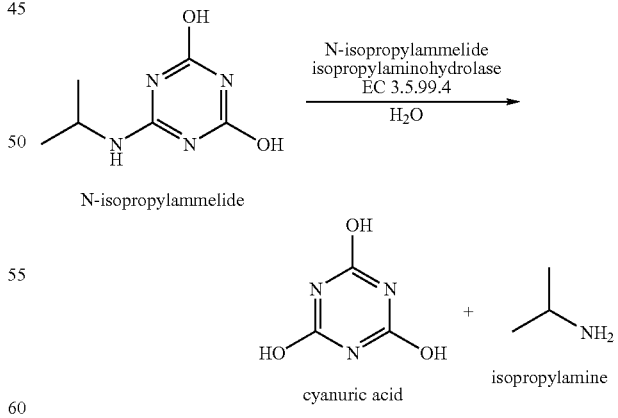

Scheme 5

For another example, both N-methylhydantoin and creatinine may serve as stabilizers of HOCl in circulating water reservoirs. These two compounds are interconverted one to the other by the catalytic conversion of creatinine deaminase (EC 3.5.4.21), which may comprise the composition-of-matter presented herein. Creatinine may in turn be enzymatically degraded to creatine by creatininase (creatinine amidohydrolase, EC 3.5.2.10), which in turn may be degraded to sarcosine and urea by creatinase (creatine amidinohydrolase, EC 3.5.3.3). The urea can be further degraded as described hereinabove.

various chemicals dissolved in it. The water-insoluble matrix allows performing a continuous and/or repetitive contact of the treated water with the enzyme, as well as maintaining the enzyme affixed, thus eliminating loss of the enzyme due to leaching out.

Scheme 6

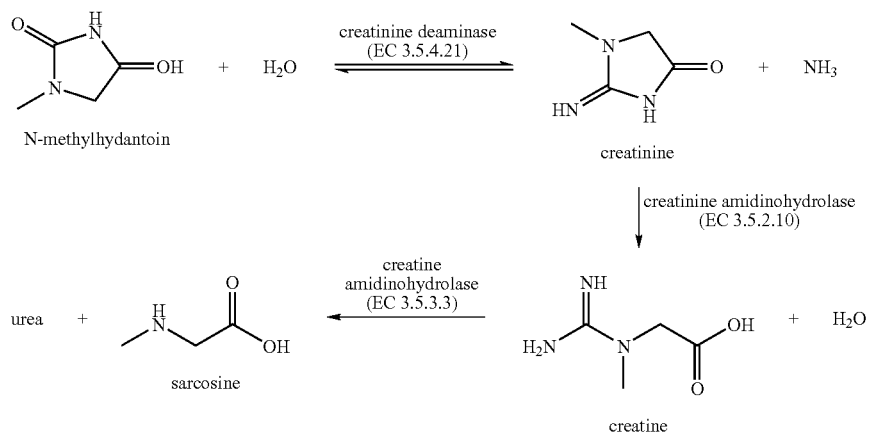

In addition to treating water of circulating water reservoirs in the context of reducing the concentration of amide-containing compounds in the water which stem from use of HOCl stabilizers, the composition-of-matter presented herein may also be used to remove from the water compounds such as urea and creatinine, which stem from human secretions, mostly in the form of urine, which is a common nuisance in public swimming pools and the likes.

In preferred embodiments, the amide-containing compound is cyanuric acid, a substrate of cyanuric acid amidohydrolase. Cyanuric acid has three amide groups in its structure, constituting an s-triazinetrione ring (its tautomer can therefore be regarded as a [1,3,5]triazine ring substituted by three hydroxyl groups at the 2, 4 and 6 positions).

A break-down product of the enzymatically-catalyzed decomposition of cyanuric acid is also an amide-containing compound; biuret ($H_3N-(C=O)-NH-(C=O)-NH_3$. As exemplified hereinabove, according to preferred embodiments, a biuret, formed upon decomposition of cyanuric acid or otherwise present in the water, can also be removed from the water by an enzymatically catalyzed decomposition to benign break-down products thereof, effected by the amidohydrolase biuret amidohydrolase.

According to preferred embodiments, a break-down product of the enzymatically-catalyzed decomposition of biuret is also an amide-containing compound; urea ($H_2N-(C=O)-NH_2$)). As exemplified hereinabove, according to preferred embodiments, urea, formed upon decomposition of cyanuric acid or otherwise present in the water, can also be removed from the water by an enzymatically catalyzed decomposition to benign break-down products, effected by the amidohydrolase urease.

The one or more enzymes selected for composing the composition-of-matter described herein is incorporated in or on a water-insoluble matrix. Such a water-insoluble matrix serves as a solid support for the enzyme, namely, it provides a stationary object, which respect to the water and the According to preferred embodiments, the water-insoluble matrix comprises a granular and/or porous substance or mixture of substances, which allows a relatively free flowing of the water therethrough.

Many commercially available solid-phase synthesis columns, purification and ion-exchange columns, are packed with granular and/or porous water-insoluble and water-permeable matrices which are suitable for protein immobilization applications, or can readily be modified so as to be suitable for protein immobilization, and therefore are suitable for use as the water-insoluble matrix in the composition-of-matter according to the present invention.

Such granular and/or porous water-insoluble matrices are well known in the art and are used in various applications such as filtration and chromatography. Representative examples include, without limitation, organic substances such as nylons, polystyrenes, polyurethanes and other synthetic polymers and co-polymers, activated carbon, cellulose, agarose, chitin, chitosan and collagen, and inorganic substances such as glass, plastic, zeolite, silica, alumina, titania, zirconia, calcium alginate and celite.

Most nylons are condensation copolymers formed by reacting equal parts of a diamine and a dicarboxylic acid, such that amide bonds are formed at both ends of each monomer in a process analogous to polypeptide biopolymers. The most common variant is nylon 6,6, also called nylon 66, in which the diamine (hexamethylene diamine) and the diacid (adipic acid) each donate 6 carbons to the polymer chain. As with other regular copolymers like polyesters and polyurethanes, the repeating unit consists of one of each monomer. Substituted diamines and dicarboxylic acids are used so as to produce nylons with a variety of free functional groups along the polymeric chain.

Polystyrene is a polymer made from the monomer styrene, a liquid hydrocarbon that is commercially manufactured from petroleum. At room temperature, polystyrene is normally a solid thermoplastic, but can be melted at higher temperature for molding or extrusion, and then re-solidified. Substituted styrene can be used to form an aromatic polymer with a variety of free functional groups along the polymeric chain.

Activated carbon (also called activated charcoal) is a general term which includes carbonaceous material mostly derived from charcoal. It denotes a material which has an exceptionally high surface area, typically determined by nitrogen adsorption, and is highly microporous. Sufficient activation for useful applications may come solely from the high surface area, though often further chemical treatment is used to enhance the adsorbing properties of the material. Chemically, activated carbon binds materials by Van der Waals force, specifically London dispersion force, and saturated active carbon can be regenerated by heating.

Cellulose is a chief constituent of the cell walls of plants (raw cotton is composed of 91% pure cellulose). Chemically, it is a long-chain polysaccharide (polymer) carbohydrate of beta-glucose. Insoluble in water and other ordinary solvents, it exhibits marked properties of absorption. Because cellulose contains a large number of hydroxyl groups, it reacts with acids to form esters and with alcohols to form ethers. Cellulose derivatives include guncotton, fully nitrated cellulose, used for explosives; celluloid (the first plastic), the product of cellulose nitrates treated with camphor; collodion, a thickening agent; and cellulose acetate, used for plastics, lacquers, and fibers such as rayon.

Chitin is one of the main components in the cell walls of fungi, the exoskeletons of insects and other arthropods, and in some other animals. It is a polysaccharide, made out of units of acetylglucosamine (more completely, N-acetyl-D-glucose-2-amine). These are linked together in β-1,4 fashion, the same as the glucose units that make up cellulose, so chitin may be regarded as a derivative of cellulose, with one hydroxyl group on each monomer replaced by an acetylamino group. This allows for increased hydrogen bonding between adjacent polymers, giving the material increased strength. The strength and flexibility of chitin is the reason it is the material of choice for surgical thread and a variety of water-insoluble matrices.

Chitosan is a linear polysaccharide composed of randomly distributed β-(1-4)-linked D-glucosamine (deacetylated unit) and N-acetyl-D-glucosamine (acetylated unit). Chitosan is produced commercially by deacetylation of chitin. The degree of deacetylation (% DA) in commercial chitosans is in the range 60-100%. The amino group in chitosan has a pKa value of about 6.5, and hence, chitosan is positively charged and soluble in acidic to neutral solution with a charge density dependent on pH and the % DA-value. Chitosan is therefore a bioadhesive which readily binds to negatively charged surfaces and compounds. Chitosan and its derivatives such as trimethylchitosan (where the amino group has been trimethylated), and quaternized chitosan have been used in delivery of therapeutic agents such as peptides and proteins, as well as for immobilizing purposes.

Zeolites is a family of hydrous aluminum silicate minerals that have high surface area and porous structure, and a highly organized three-dimensional structure of tetrahedral $SiO_4$ and $AlO_4$ linked to one another by a shared oxygen. More than 150 zeolite types have been synthesized and 48 naturally occurring zeolites are known. They are basically hydrated alumino-silicate minerals with an open structure that can accommodate a wide variety of positive ions, such as $Na^+$, $K^+$, $Ca^{2+}$, $Mg^{2+}$ and others. These positive ions are rather loosely held and can readily be exchanged for others in a contact solution. Some of the more common mineral zeolites include analcime, chabazite, heulandite, natrolite, phillipsite, and stilbite. An example mineral formula for natrolite is $Na_2Al_2Si_3O_{10}.2H_2O$. Zeolites can be modified by thermal and chemical treatments such as cation exchange or dealumination. The modified zeolites give the possibility of creating and regulating acid-base, hydrophobic-hydrophilic, and selective adsorption properties that are responsible for their structural diversity and extensive applications in catalytic reaction. Due to their high stability, porous structure and chemical diverseness of their surface, zeolites and surface modified derivatives thereof are used as molecular filters, chromatography, ion-exchange agents and for immobilizing enzymes and other proteins.

Other forms of organic polymers, copolymers and cross-linked derivatives thereof, and inorganic materials such as diatomaceous earths and other types of molecular sieves, typically used in various water filtrations, can be used as a granular and/or porous water-insoluble matrix, according to the present invention, on or in which an enzyme can be incorporated.

The term "incorporated", as used herein, refers to any mode of contact between the water-insoluble matrix and the enzyme which achieves immobilization of the enzyme with respect to the matrix, thus rendering a biochemically active enzyme insoluble, or in other words immobilized, and in some cases more protected, thus more stable than the soluble enzyme.

Incorporation of an enzyme in or on the matrix can be effected by attachment via any type of chemical bonding, including covalent bonds, ionic (electrostatic) bonds, hydrogen bonding, hydrophobic interactions, metal-mediated complexation, affinity-pair bonding and the likes, and/or by attachment via any type of physical interaction such as magnetic interaction, surface adsorption, encapsulation, entrapment, entanglement and the likes.

The enzyme(s) can be incorporated in and/or on physical structural elements of a water-insoluble matrix. In cases where the structural elements of the matrix are granular but not porous, such as, for example, in cases where the matrix is made of solid glass beads or particles, or solid plastic beads or particles, the enzyme(s) is incorporated on the surface of the beads or particles, and the water that flows in the channels between the beads or particles comes in contact with the enzyme(s), thus allowing the amide-containing compounds dissolved in the water to be enzymatically degraded.

In cases where the structural element of the matrix is porous but not granular, such as, for example, in cases where the matrix is extruded zeolite blocks, carbonaceous blocks or solid plastic foam blocks, the enzyme(s) is incorporated in the cavities, on the inner surface of the innate interconnected pores and channels which are characteristic to such matrices, as well as on the outer surface of the block, and the water that flows in the inter-connected pores and channels comes in contact with the enzyme(s).

In cases where the structural elements of the matrix are granular and porous, such as, for example, in cases where the matrix is zeolite granules or molecular sieves pellets, the enzyme(s) is incorporated on the surface of the granules or pellets and in the inner surface of the pores and channels of these matrices, and the water that flows between the granules or pellets as well as through them comes in contact with the enzyme(s), thus allowing the amide-containing compounds dissolved in the water to be enzymatically degraded.

In preferred embodiments, the incorporation of the enzyme to the water-insoluble matrix is effected by a combination of chemical and physical attachments such as covalent bonding and entanglement.

In preferred embodiments of the present invention, the incorporation of the enzyme to the water-insoluble matrix is effected by covalently attaching the enzyme to the water-insoluble matrix (the solid support) by conventional methods known in the art for enzyme immobilization.

Exemplary immobilization techniques are described for example in U.S. Pat. Nos. 4,071,409, 4,090,919, 4,258,133, 4,888,285, 5,177,013, 5,310,469, 5,998,183, 6,905,733, and 6,987,079, U.S. Patent Application Publication No. 2003/0096383, and in Yan A-X. et al, 2002, *Applied Biochemistry and Biotechnology*, Vol. 101(2), pp. 113-130(18); and Ye, Yun-hua et al., 2004, *Peptide Science*, Vol. 41, pp 613-616, which are incorporated herein by reference as if fully set forth.

Briefly, protein immobilization by covalent bonding to a solid matrix, according to preferred embodiments of the present invention, is based on coupling two functional groups, as these are defined hereinbelow, one within the matrix (e.g., on its surface) and the other within the enzyme (e.g., on its surface), either directly or via a spacer. The spacer can be, for example, a bifunctional moiety, namely, a compound having at least two functional groups which are capable of forming covalent bonds with functional groups of both the matrix and the enzyme.

As used herein, the phrase "functional group" describes a chemical group that has certain functionality and therefore can participate in chemical reactions with other components which lead to chemical interactions as described hereinabove (e.g., a bond formation).

Non-limiting examples for functional groups which are commonly found in proteins and can be utilized for direct or indirect coupling with a solid support matrix include both functional groups derived from side chains of certain amino-acid residues and functional groups derived from the N-terminus or the C-terminus of the protein. These include, for example, hydroxyl (stemming from side-chain of the amino-acids serine and tyrosine), amine (stemming from side-chain of the amino-acids lysine and arginine, and the N-terminus), carboxyl (stemming from side-chain of the amino-acids glutamate and aspartate, C-terminus) and thiol (stemming from side-chain of the amino-acid cysteine).

Other functional groups can be introduced to the protein by natural processes such as post-translationally added residues. These include, for example, glycans, lipids, phospholipids, phosphates and the likes. Other functional groups can also be introduced to the protein by modifications which are genetically engineered the amino-acid composition of the protein. Further still, functional groups may be introduced chemically to a native, post-translationally modified and/or genetically engineered proteins by non-denaturing processes. Representative examples of such functional groups include, without limitation, amine, acyl, aldehyde, alkoxy, thioalkoxy, alkyl, alkenyl, C-amide, N-amide, carboxyl, diol, farnesyl, geranylgeranyl, guanidine, hydroxy, thiohydroxy, imidazole, indole, phosphate and sulfate, as these are defined herein.

Non-limiting examples for functional groups which exist on the surface of the water-insoluble matrix material, or can be introduced thereto, and can be utilized for direct or indirect conjugation with an enzyme include, without limitation, hydroxyl (present on the surface of organic and inorganic matrices containing silica, alumina and other metal oxides), amine (which can be chemically introduced to many inorganic matrices), acyl, aldehyde, alkoxy, thioalkoxy, alkyl, alkenyl, C-amide, N-amide, carboxyl, diol, farnesyl, geranylgeranyl, guanidine, hydroxy, thiohydroxy, imidazole, indole, phosphate and sulfate.

As used herein, the term "hydroxy" refers to an —OH group.

As used herein, the term "thiohydroxy" or "thiol" refers to an —SH group.

As used herein, the term "carboxyl" refers to a —C(=O)OR' group, where R' is as defined herein.

As used herein, the term "aldehyde" refers to a —C(=O)—H group.

As used herein, the term "diol" refers to a vicinal diol which is a —CR'(OH)—CR"(OH)— group. Glycan, which can be attached to a protein during a post-translational glycosilation, are abundant with diol groups.

As used herein, the term "carbonyl" refer to a —C(=O)-alkyl group, as defined hereinabove.

The term "alkoxy" as used herein describes both an —O-alkyl and an —O-cycloalkyl, as defined hereinabove.

As used herein, the term "thioalkoxy" describes both a —S-alkyl, and a —S-cycloalkyl, as defined hereinabove.

The term "farnesyl", as used herein, refers to the fatty residue of fernesene, typically attached to post-translationally modified cysteine residues at the C-terminus of proteins in a thioether linkage (—C—S—C—).

The term "geranylgeranyl", as used herein, refers to the fatty residue of geranylgeranene, typically attached to post-translationally modified cysteine residues at the C-terminus of proteins in a thioether linkage.

The term "guanidine" refers to a —NR'C(=NR")—NR'"R* group, where R' and R" are as defined herein and R'" and R* are defined as either R' or R". In the context of the present invention, guanidine is a functional group on the side-chain of the amino-acid arginine, therefore it is preferably —NH—C(=NH)—NH$_2$.

As used herein, the term "imidazole" refers to the five-membered heteroaryl group that includes two non-adjacent nitrogen atoms. An imidazole residue can be found in the side-chain of the amino acid histidine.

As used herein, the term "indole" refers to refers to a bi-cyclic heteroaryl comprised of fused phenyl and pyrrole groups. An indole residue can be found on the side-chain of the amino acid tryptophan.

The term "phosphate" describes a —O—P(=O)(OR')(OR") group, with R' and R" as defined herein. Phosphate groups can be attached to a protein during a post-translational phosphorylation process by kinases. Reversible protein phosphorylation, principally on serine, threonine or tyrosine residues, is one of the most important and well-studied post-translational modifications.

As used herein, the term "sulfate" refers to a —O—S(=O)$_2$ —O—R', with R' as defined herein. Modification of proteins with sulfate occurs typically at tyrosine residues, and the universal sulfate donor is 3'-phosphoadenosyl-5'-phosphosulphate.

According to preferred embodiments, the incorporation of the enzyme to the water-insoluble matrix is effected by a cross-linking agent which forms covalent bonds between functional groups on the surface of the matrix and the surface of the enzyme, and optionally further between molecules of the cross-linking agent itself, thereby forming an entanglement of threads of residues of the cross-linking agent. In these preferred embodiments, incorporation of the enzyme to the water-insoluble matrix is effected by a combination of chemical bonding of the enzyme to the matrix via residues of the cross-linking agents, and entanglement of the enzyme in a web of threads made of residues of the cross-linking agent.

The phrase "cross-linking agent", as used herein, refers to a bifunctional compound that can promote or regulate intermolecular interactions between polymer chains, linking them together to create a more rigid structure. Cross-links are bonds linking functional groups of polymers and/or other substances, so as to form intermolecular interactions therebetween and, as a result, a three-dimensional network interconnecting these substances. Cross-linking can be effected via covalent bonds, metal complexation, hydrogen bonding, ionic bonds and the like.

Exemplary cross-linking agents that are suitable for use to effect covalent cross-linking include, without limitation, polyaldehydes such as glutaraldehyde, polycarboxylic acids or anhydrides, polyamines, epihalohydrins, diepoxides, dialdehydes, diols, carboxylic acid halides, ketenes and like compounds.

A presently preferred cross-linking agent, according to embodiments of the present invention is glutaraldehyde. As described in detail in the Examples section that follows, glutaraldehyde readily forms an imine bond with amine groups under mild conditions.

The composition-of-matter presented herein can be incorporated in a water treatment device, so as to affect water treatment, as described herein.

Thus, according to another aspect of the present invention there is provided a device for water treatment which includes at least one casing having the composition-of-matter presented herein embedded therein such that water flowing through the casing becomes in contact with the composition-of-matter, such that reducing the concentration of at least one amide-containing compound in the water is effected.

Water-treatment devices that are suitable for use in the context of the present invention are described, for example, in U.S. Pat. Nos. 4,532,040, 4,935,116, 5,055,183, 5,478,467, 5,855,777, 5,980,761, 6,257,242 and 6,325,929, which are incorporated by reference as if fully set forth herein.

Water treatment devices utilized in circulating reservoirs typically form a part of a larger system, which is typically referred to as a water plant.

Typical water treatment devices used in water plants of circulating reservoirs exert their designated treatment action when water flows therethrough, either by means of a pump or by gravity. The water flows into the system, enters the device, and passes through a water-permeable and water-insoluble matrix within the device, which effects the designated treatment action, typically filtration of insoluble particulates and objects, chemical exchange of solutes and ions and dissolution and addition of chemicals into the water.

The device containing the composition-of-matter described herein can therefore be any device, or part of a device through which water flows during the process of treating the water. Such a device can be, for example, one or more of a filter, a filter cartridge, an ion-exchanger, an erosion feeder and the likes, as is exemplified hereinunder.

Thus, according to preferred embodiments, the composition-of-matter of the present invention can be added to a water-treatment device having a water-treatment substance embedded therein which effects the originally designated treatment action of these devices, or replace that substance altogether.

The device, according to the present embodiments, can form a part of a comprehensive water treatment system, which exerts other water treatment actions, such as filtration of solid particulates and addition of chemicals. Water that flows through such a water-treatment system also flows through the device presented herein. The system can be design such that all its water capacity flows through the device, or such that only a part of its water capacity flows therethrough.

Typically the flow rate can be adjusted per device for the optimal function of the system and every device in it. For an efficient function of the present device, which includes an immobilized active enzyme, the amount of enzyme, amount of water-insoluble matrix, overall shape of the device and flow-rate need to be designed to as to suit the system's layout, water capacity (power) and the expected rate at which the concentration of an amide-containing compound such as, for example, cyanuric acid, is required to be reduced. The rate of an amide-containing compound reduction depends on the enzymatically catalyzed reaction condition, e.g., temperature, pH, ionic strength and, in relevance to this case, water flow. All the abovementioned parameters are considered while designing the device.

The incorporation of enzymes to water-insoluble matrices is typically measured in international units of activity. An international unit (IU) of an enzyme is defined as the amount of enzyme that produces one micromole of a reaction product in one minute under defined reaction conditions. The amount of IU which can be incorporated to a matrix depends on the type of matrix and incorporation technique, surface area of the matrix, the availability and chemical reactivity of functional groups suitable for conjugation in both the enzyme and the matrix, and on the residual enzymatic activity subsequent to the incorporation process. Typical enzyme load ranges from a few IU to hundreds of IU of an enzyme per $cm^3$ of matrix material. An optimal load, namely, the optimal amount of enzyme to be incorporated per a unit volume of water-insoluble matrix material, is an example of one parameter that is considered while designing the device.

The water-treatment device presented herein is therefore preferably shaped and sized, and its through-flow is designed, so as to achieve optimized efficacy in reducing the concentration of the desired amide-containing compound (e.g., cyanuric acid).

For example, using the enzymatic catalysis parameters presented hereinabove for cyanuric acid amidohydrolase, one can calculate that for a water quantum of 100 cubic meters, 250 mg of cyanuric acid amidohydrolase is capable of treating t this water quantum by decreasing the cyanuric acid concentration from 100 ppm to 50 ppm within a time period of 20.8 hours. Considering typical water pumps used in water treatment systems of pools, which can transfer an average of 11 cubic meters per hour, this water quantum will be treated by 250 mg of cyanuric acid amidohydrolase once in 9.09 hours and more than twice in 20.8 hours, which is an acceptable rate of cyanuric acid degradation.

A reduction of 50 ppm in cyanuric acid concentration translates to approximately 50 grams of cyanyric acid (about 0.4 moles) per cubic meter of water at chlorine-lock conditions. Therefore, about 280 IU of cyanuric acid amidohydrolase are required in order to reduce the concentration of cyanuric acid in one cubic meter of water within a time period of 24 hours.

As used herein, the term "about" means±10%.

Thus, according to preferred embodiments of the present invention the amount of cyanuric acid amidohydrolase required to treat one cubic meter of water within a time period of 24 hours ranges from 0.5 mg to 10 mg per, preferably 1 to 5, and more preferably the amount of cyanuric acid amidohydrolase is at least 2.5 mg per one cubic meter of treated water.

As mentioned hereinabove, in the water-treatment device described herein, the composition-of-matter presented herein is embedded in a casing.

The casing is required so as to avoid sweeping of the composition-of-matter by the water passing through the device. Another purpose of a casing is to form the desired shape and cross-section of the device, which will optimize its function and maintain a continuous, void-free bed of the composition-of-matter presented herein.

The casing material is preferably selected suitable for water high-pressure, and is typically water-insoluble and water-tight. Furthermore, the casing material is preferably selected inactive and stable with respect to water and the chemicals that are typically found in circulating reservoirs. Examples for suitable casing materials include, without limitation, plastic, galvanized metal and glass.

In preferred embodiments, the device for water treatment of the present invention includes a casing with two parallel perforated faces, constituting a semi-closed compartment, whereby the composition-of-matter presented herein fills, or partially fills the compartment. The casing thus has one perforated face for a water inlet, and the other perforated face for a water outlet. The water to be treated (containing the amide-containing compound(s)) enters the inlet, pass through the compartment containing the composition-of-matter, and come in contact with the permeable and water-insoluble matrix having the enzyme(s) incorporated therein or thereon.

An exemplary device, according to preferred embodiments of the present invention, is a water-treatment column. FIG. 1 present a simplified illustration of a typical water-treatment column. A water-treatment column 10, designed to lower the concentration of cyanuric acid in water, is composed of a pressure-resistant casing 12 typically having a round or elliptic cross-section, which is bounded by an upstream perforated face 14 connecting an upstream cap 16 and a downstream perforated face 18 connecting a downstream cap 20. The untreated water having a high concentration of cyanuric acid, marked in FIG. 1 by a spotted arrow, enters water-treatment column 10 from an upstream pressure-resistant inlet 22, designed for attaching water-treatment column 10 in-line with a water-treatment system. The treated water, having a lower concentration of cyanuric acid and marked in FIG. 1 by a clear arrow, exit water-treatment column 10 from a downstream pressure-resistant outlet 24, and therefore come in contact and flow through a composition-of-matter, according to the present invention, comprised of water-permeable and water-insoluble matrix 26 and a cyanuric acid amidohydrolase 28 attached thereto which effects the reduction of cyanuric acid in the water.

Another exemplary device according to preferred embodiments of the present invention is a triple-action water-treatment cartridge. Such triple-action cartridge may exert three different water-treatment activities, one after the other, as water flows from one separated sub-compartment in the device to another. In the context of the present invention, each sub-compartment may house a different composition-of-matter, each comprising a different enzyme. Alternatively, two sub-compartments house different compositions-of matter according to the present invention, while the third sub-compartment exerts a water-filtration action, or acts as an erosion feeder element for adding a slow-dissolving chemical to the water, etc.

FIG. 2 presents a simplified illustration of a triple-action water-treatment cartridge. A triple-action water-treatment cartridge 30, designed to effect total degradation of cyanuric acid, is encased in a casing 32, which also line an inner cavity 34 which allows the untreated water, having a high concentration of cyanuric acid and marked in FIG. 2 by spotted arrows, to flow though triple-action water-treatment cartridge 30 and reach an upstream perforated face 36 where the untreated water enters triple-action water-treatment cartridge 30 and into a first sub-compartment 50 where the untreated water comes in contact and flow through a first composition-of matter 38, comprising cyanuric acid amidohydrolase. The now singly treated water, having the cyanuric acid decomposition product biuret in it, passes through a perforated wall 40 and enters the second sub-compartment 52 to come in contact and flow through second composition-of matter 42 comprising biuret amidohydrolase. The now doubly treated water, having the biuret decomposition product urea in it, passes through a perforated wall 44 and enters the third sub-compartment 54 to come in contact and flow through a third composition-of matter 46 comprising urease. The triply-treated water, having a lower concentration of cyanuric acid and its break-down products, marked in FIG. 2 with clear arrows, exits triple-action water-treatment cartridge 30 through a downstream perforated face 48, and re-enter the water-treatment system.

Other exemplary device for water treatment according to preferred embodiments of the present invention may be a filter cartridge, similar to that disclosed, for example, in U.S. Pat. No. 6,325,929, and containing, as the composition-of-matter, an extruded solid, water-permeable carbonaceous material block as a water-insoluble matrix and one or more amidohydrolase enzyme(s) incorporated in and on the carbonaceous block.

As mentioned hereinabove, the incorporation of an amidohydrolase to a water-insoluble matrix enables the construction of a device for reducing the concentration of at least one amide-containing compound in the water of circulating reservoirs.

Hence, according to another aspect of the present invention, there is provided a method of treating water which is effected by contacting water with a water treatment device, as presented hereinabove.

The water treatment is effected by bringing the water in contact with the composition-of-matter presented herein. In order for the treatment to be effective, it is desirable that the water would flow at a certain rate so as to come in contact with an effective amount of the amidohydrolase for a certain period of time.

As mentioned above, the device may form a part of a more comprehensive water treatment system which can house the device and effect water flow through the device by means of, for example, water pumps, distribution manifolds, hoses and pipes, spigots and valves.

Thus, according to preferred embodiments of this aspect of the present invention, the method is effected by passing the water through the device to thereby effect the reduction of the concentration of at least one amide-containing compound in the water.

As presented hereinabove, a detrimental phenomenon of chlorine-lock occurs when the concentration of the stabilizer, cyanuric acid, reaches 100 ppm; rendering the quality of the water in the circulating reservoir unacceptable. Thus, an efficient and effective water treatment, according to the present in invention, includes the reduction of the concentration of cyanuric acid below 100 ppm. Preferably, reduction of the concentration of cyanuric acid is effected so as to achieve a concentration of cyanuric acid that ranges between about 30 ppm and about 70 ppm, with an ideal and most preferable concentration of 50 ppm.

In addition to treating the water of circulating reservoirs so as to reach the desired concentration of cyanuric acid in the water, it is important that the desired effect of water treatment would be achieved within a relatively short period of time. The time period should be minimized so as to avoid loss of operational time of circulating reservoir, and avoid the risk of reaching chlorine-lock due to the continuous addition of stabilized sanitizers. The length of the time period within which the treatment takes place depends on the amount of water to be treated, the capacity of the water-treatment system and the amount and the catalytic efficiency of the enzyme, as discussed hereinabove.

To demonstrate an exemplary implementation of the method of treating water according to the present invention, one can consider an exemplary circulating reservoir such as an Olympic swimming pool. An Olympic swimming pool which meets international standards as defined by The International Swimming Federation (abbreviated FINA for the French name Fédération Internationale de Natation), must be 50 meters in length by 25 meters wide by at least 2 meters in depth. Among other standards, the water must be kept at 25-28° C. and the lighting level at greater than 1500 lux. There are thus at least 2500 cubic meters of water (660,430 U.S. liquid gallons) which must be treated in a standard Olympic pool.

Using the calculation for the sufficient amount of cyanuric acid amidohydrolase needed to treat 100 cubic-meters of water, i.e., to reduce the cyanuric acid concentration from 100 ppm to 50 ppm within about 20 hours, as presented hereinabove, the water of an Olympic pool in a state of chlorine-lock should be passed twice through one or more devices, as presented herein, and be brought in contact with a composition-of-matter comprising cyanuric acid amidohydrolase, according to the present invention, which contain a total of at least 6.25 grams of the enzyme.

The present invention also envisages treating water using non-immobilized (i.e., soluble) enzymatic compositions of the present invention, albeit with modifications in enzyme concentration for treating large volume of water (e.g., swimming pool).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

As discussed hereinabove, methods of immobilizing active enzymes on solid support materials while retaining, and in some cases enhancing their biochemical catalytic activity, are well known in the art and are presented in numerous publications such as U.S. Pat. Nos. 4,071,409, 4,090,919, 4,258,133, 4,888,285, 5,177,013, 5,998,183, 6,905,733, and 6,987,079 and U.S. Patent Application No. 2003/0096383, and other publications such as Yan A-X. et al., 2002, *Applied Biochemistry and Biotechnology*, Vol. 101(2), pp. 113-130(18); and Ye, Yun-hua et al., 2004, *Peptide Science*, Vol. 41, pp 613-616.

Example 1

Immobilization of Cyanuric Acid Amidohydrolase on Silica Gel

Immobilization of cyanuric acid amidohydrolase on silica gel is performed based on a procedure described in U.S. Pat. No. 4,888,285.

Silica gel (having particle diameter of 0.3 μm and an average pore diameter of 500 Å) is aminated with γ-aminotriethoxysilane in toluene to prepare the $SiO_2$—$NH_2$ solid support matrix.

A commonly used conjugation method, typically performed under mild, non-denaturing conditions suitable for enzymes, is the well established Schiff-base (imine) formation between amines and aldehydes (see, Scheme 7 below). This universal conjugation method can be carried out readily under physiological, mild conditions, as described by Merril et al. [*Science*, 1981, 211, pp. 1437-1438].

Scheme 7

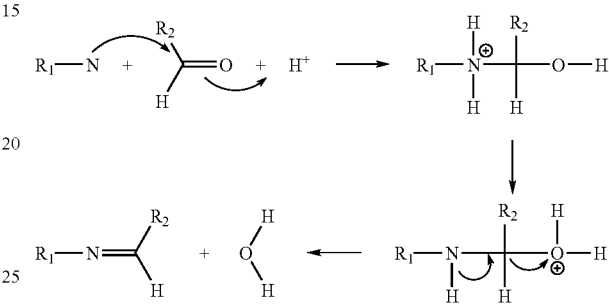

Thus, an immobilization solution of cyanuric acid amidohydrolase (E.C. 3.5.2.15, 1500 U/ml) and glutaraldehyde 1.0-10% (w/v) in TRIS/HCl buffer (0.05 M, pH 8), is contacted with 10 ml of the aminated silica gel (SiO2-NH2, 1 ml) at room temperature for 4 hours, so as to covalently conjugate the enzyme, via naturally occurring amine groups (lysine residues) to the aminated silica matrix via the bisfunctional glutaraldehyde (bis-aldehyde), and thereby carry out the conjugation of the enzyme to the immobilization solid support matrix.

Thereafter, the treated matrix is washed with TRIS/HCl buffer (0.05 M, pH 8) to remove unbound enzyme and glutaraldehyde and the resulting immobilized enzyme is recovered by vacuum filtration. The recovered enzymesilica powder is dried overnight at room temperature.

The fraction of the available cyanuric acid amidohydrolase transferred onto the silica gel solid support matrix is determined by comparing the initial cyanuric acid amidohydrolase activity in the immobilization solution with the activity after the immobilization process is completed. Specific activity of cyanuric acid amidohydrolase is assayed according to the method disclosed by David M. et al. in *Biocatalysis and Biotransformation*, 2005, Vol. 23(6), pp 387-96.

Example 2

Immobilization of Cyanuric Acid Amidohydrolase on Crystalline Sodium Aluminosilicate Zeolite A Immobilization of cyanuric acid amidohydrolase on crystalline sodium aluminosilicate (zeolite A) is performed based on a procedure described in U.S. Pat. No. 5,998,183.

A glutaraldehyde/buffer solution is prepared by mixing glutaraldehyde in 0.050 M TRIS/HCl buffer to produce a pH 8 buffer solution containing 1% (w/v) glutaraldehyde.

Sodium aluminosilicate (zeolite A, 20 mg) is mixed with 50 ml of the glutaraldehyde/buffer solution described above, and the resulting mixture is incubated at 20° C. for four hours. The mixture is then washed with HPLC grade water, and the remaining modified zeolite is recovered by vacuum filtration. The recovered zeolite is dried overnight at room temperature, and weighed.

An enzyme immobilization solution is prepared by dissolving 8000 units of cyanuric acid amidohydrolase (E.C. 3.5.2.15) in 100 ml of 0.050 M TRIS/HCl buffer (pH 8.0).

The recovered modified zeolite is incubated in 5 ml of the enzyme immobilization solution at 20° C. for 8 hours, under gentle stirring, so as to affect conjugation of the enzyme to the modified zeolite via Schiff base formation, as described hereinabove. The mixture is then washed with 0.050 M TRIS/HCl buffer (pH 8.0), and the resulting immobilized enzyme is recovered by vacuum filtration. The recovered enzyme-zeolite powder is dried overnight at room temperature.

The fraction of the available cyanuric acid amidohydrolase transferred onto the zeolite solid support matrix is determined by comparing the initial cyanuric acid amidohydrolase activity in the immobilization solution with the activity after the immobilization process is completed, as described in Example 1 hereinabove.

Example 3

Immobilization of Cyanuric Acid Amidohydrolase on Nylon

Immobilization of cyanuric acid amidohydrolase on nylon is performed based on a procedure described in U.S. Pat. No. 5,310,469.

Nylon beads (having particle diameter of 0.3 μm) are treated with hydrochloric acid so as to partially hydrolyze amide bonds of the polyamide matrix surface to thereby obtain free amine groups on the surface of the solid support matrix.

An immobilization solution of cyanuric acid amidohydrolase (1500 U/ml) and glutaraldehyde 1.0-10% (w/v) in TRIS/HCl buffer (0.05 M, pH 8), is contacted with a sample of the partially hydrolyzed nylon beads at room temperature for 4 hours, so as to affect the conjugation of the enzyme to the immobilization solid nylon support matrix via Schiff base formation, as described hereinabove.

Thereafter, the treated matrix is washed with TRIS/HCl buffer (0.05 M, pH 8) to remove unbound enzyme and glutaraldehyde and the resulting immobilized enzyme is recovered by vacuum filtration. The recovered enzyme-nylon beads are dried overnight at room temperature.

The fraction of the available cyanuric acid amidohydrolase transferred onto the nylon beads is determined by comparing the initial cyanuric acid amidohydrolase activity in the immobilization solution with the activity after the immobilization process is completed, as described in Example 1 hereinabove.

Example 4

Immobilization of Biuret Amidohydrolase to a Solid Support

In this example, biuret amidohydrolase (E.C. 3.5.1.84) is attached to a solid support such as silica gel, zeolite or nylon beads, essentially as described above in Examples 1, 2 and 3.

Example 5

Immobilization of Urease to a Solid Support

In this example, urease (E.C. 3.5.1.5) is attached to a solid support such as silica gel, zeolite or nylon beads essentially as described above in Examples 1, 2 and 3.

Example 6

Cloning and Overexpression of Cyanuric Amidohydrolase (TrzD) with a his Tag

In order to facilitate preparation of large amounts of enzyme, cyanuric amidohydrolase (TrzD) was isolated from *Pseudomonas* sp NRRLB 12227 via PCR using primers designated as SEQ ID Nos.: 2 and 3 (see also FIG. 3) with a PCR program as detailed in FIG. 3. The PCR primers provide sticky ends for directional ligation into an XhoI/NdeI digested plasmid.

FIG. 5 depicts the resultant PCR fragment of approximately 1200 bp under electrophoresis in a 1% agarose with molecular weight markers in an adjacent lane. Visualization is by ethidium bromide staining. The TrzD PCR product excised from the gel and purified from the agarose.

FIG. 6 is a simplified flow diagram illustrating an exemplary cloning procedure 600 of isolated TrzD PCR product 630 into a pET41a plasmid 610. (Novagen; EMD Biosciences Inc.; San Diego, Calif.; USA)

The pET41 plasmid adds a his tag (SEQ ID No.: 1 at the C terminal of the TrzD protein. The his tag allows the purification of the protein by affinity chromatography on a Ni column so that a scaleable source of enzyme becomes available for further characterization.

In order to facilitate directional ligation 640, PCR fragment 630 and plasmid 610 were each digested with XhoI and NdeI (632 and 620 respectively).

After Ligation 640, the resultant TrzD-pET41a plasmid was transformed 650 into *E. coli* DH5α. Transformed bacterial colonies were grown 660 under Kanamycin selection and representative clones were subject to PCR analysis. PCR positive plasmids were isolated and subject to DNA sequencing 662 for validation. The C terminus of TrzD with and without the added his tag is presented in FIG. 4 which depicts SEQ ID Nos.: 1, 4, 5, 6 and 7 and explains the relationship therebetween at both nucleic acid and amino acid levels.

Selected clones were re-transformed 664 into *E. coli* BL21. Colonies were again grown under Kanamycin selection and analyzed by PCR 666. Expression of cyanuric amidohydrolase (TrzD) was induced 668 with IPTG.

Example 7

Purification of Cyanuric Amidohydrolase (TrzD) with a his Tag

Bacteria transformed 664 with TrzD-pET41a and induced 668 with IPTG according to Example 6 provide a scaleble source of his-tagged enzyme.

FIG. 7 illustrates an exemplary purification procedure 700 for recovery of the enzyme from bacterial culture induced with IPTG (668; see FIG. 6). Briefly, bacteria are treated with benzonase 770 to disrupt the cell membrane and produce a homogenate. Centrifugation 772 produces an insoluble protein fraction 780 which is discarded and a soluble protein fraction 790 containing the desired enzyme.

Soluble protein fraction 790 is subject to affinity chromatography 792 on a nickel column. The his tagged enzyme is allowed to bind to the column. Other soluble proteins are washed away and the his-tagged Trzd enzyme is eluted 794 as a pure protein using imidazole. Dialysis to remove imidazole produces a pure protein 796

FIG. 8 is a Coomassie stained SDS-polyacrylamide gel illustrating various stages of purification of TrzD as outlined in FIG. 7. Lane 1 is a prestained protein molecular weight Ladder. Lane 2 is a total cell lysate resulting from benzonase treatment (770). Lane 3 is the soluble protein fraction (790). Lane 4 is flow through from the nickel column representing unbound proteins. Lane 5 is purified his-tagged TrzD (796) eluted from the column with imidazole.

Example 8

Characterization of Cyanuric Amidohydrolase (TrzD) with a his Tag

TrzD with a his tag prepared and isolated according to Examples 6 and 7 was characterized with respect to enzymatic activity using accepted techniques. The recombinant his tagged TrzD enzyme is characterized by a Vmax of 0.3 µmoles/min/mg. It is possible that presence of the his tag at the C terminus of TrzD contributes to the observed low Vmax. For commercial development, a source of enzyme with a higher Vmax can be an advantage. Optional ways of large scale preparation of TrzD enzyme include, but are not limited to, using an affinity purification tag which does not interfere with enzyme activity and/or scaling up production of wild type enzyme (e.g. using a size fractionation strategy). It is noted that purification of TrzD protein to complete homogeneity is not a requirement for the proposed use since the prepared enzyme will be immobilized on a solid substrate. Optionally, there is a trade-off between purification cost and efficiency of a device containing the immobilized enzyme on solid substrate.

Despite the low activity, availability of the recombinant his tagged TrzD enzyme facilitates assessment of effect of normal swimming pool conditions on TrzD.

Example 9

Sensitivity of Cyanuric Amidohydrolase (TrzD) to Free Chlorine

TrzD with a his tag prepared and isolated according to Example 6 was characterized with respect to sensitivity to free chlorine in order to evaluate its suitability for use under swimming pool conditions.

FIG. 9 summarizes the results graphically. Briefly, the recombinant TrzD was incubated at room temperature at different concentrations of free Cl solutions (0-5 ppm as indicated) for 4 days. Enzymatic activity was measured at pH=8 and T=30° C.

Enzymatic activity was monitored by following the decrease of absorbance at 220 nm and measuring the slope. The slope is indicative of the amount of cyanuric acid degraded over a given time period Results are expressed as % of the 0 ppm activity. Chlorine concentrations in the range of 0.1 to 5 ppm caused no significant change in activity relative to 0 ppm of free chlorine. These results indicate that chlorine concentrations typically found in a swimming pool do not significantly inhibit Trzd activity.

Example 10

Sensitivity of Cyanuric Amidohydrolase (TrzD) to Biuret

TrzD with a his tag prepared and isolated according to Example 6 was characterized with respect to sensitivity to biuret in order to evaluate its suitability for use under swimming pool conditions.

FIG. 10 summarizes the results graphically. Briefly, recombinant Trzd was incubated at room temperature at different concentrations of Biuret (0-250 ppm as indicated) for 3 days. Enzymatic activity was measured at pH=8 and T=30° C. as in Example 9. Results are expressed as % of the 0 ppm activity. Biuret concentrations in the range of 0.1 to 185 ppm caused no significant change in activity relative to 0 ppm of free biuret. 250 ppm of biuret caused a 60% inhibition of enzymatic activity.

These results indicate that biuret concentrations typically found in a swimming pool (185 ppm or less) do not significantly inhibit Trzd activity.

Example 11

Sensitivity of Cyanuric Amidohydrolase (TrzD) to Simulated Swimming Pool Conditions In order to confirm the results of examples 9 and 10, TrzD with a his tag prepared and isolated according to Example 6 was characterized with respect to sensitivity simulated swimming pool conditions.

FIG. 11 summarizes the results graphically. Briefly, recombinant Trzd was incubated under simulated swimming pool conditions (pH=7.2, free Cl 5 ppm, Alkalinity 120 ppm, Biuret 185 ppm and T=26° C.) for 3 days. Incubation in distilled water served as a control. Enzymatic activity was monitored as in Examples 9 and 10.

These results confirm that even extreme swimming pool conditions do not significantly inhibit the enzymatic activity of His-tagged Trzd activity. (typical swimming pool conditions do not significantly inhibit Trzd activity)

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating chlorinated water used in a circulating water reservoir, the method comprising passing the chlorinated water through a device comprising at least one casing having embedded therein a composition-of-matter comprising a water-insoluble matrix and, covalently attached thereto directly or via a spacer, both cyanuric acid amidohydrolase and biuret amidohydrolase, such that circulating chlorinated water flowing through said casing comes into contact with said composition-of-matter, so as to reduce a concentration of both cyanuric acid and biuret in the water, thereby treating the chlorinated water.

2. The method of claim 1, further comprising:
monitoring said concentration of said cyanuric acid in said chlorinated water; and maintaining said flowing until said concentration of said cyanuric acid in said water reaches a value less than 100 ppm.

3. The method of claim 2, wherein an amount of said cyanuric acid amidohydrolase required to reach said value in one cubic meter of said water within a time period of 24 hours is at least 2.5 mg per one cubic meter of said water.

4. The method of claim 1, wherein the water treatment is effected during a time period of 20 hours or less.

5. The method of claim 1, wherein passing said water through said device is effected at a flow rate of at least 10 cubic meters per hour.

6. The method of claim 1, wherein said circulating water reservoir is for use by humans.

7. The method of claim 1, wherein said circulating water reservoir is selected from the group consisting of a pool, an artificial pond or lake, a swimming pool, a spa, a hot-tub, a whirlpool bath, a fountain and a waterslide.

8. A method of treating chlorinated water used in a circulating water reservoir, the method comprising passing the chlorinated water through a device comprising at least one casing having embedded therein a composition-of-matter comprising a water-insoluble matrix and, covalently attached thereto directly or via a spacer, all amidohydrolase enzymes necessary to hydrolyze cyanuric acid all the way to $CO_2$ and $NH_3$ molecules, such that circulating chlorinated water flowing through said casing comes into contact with said composition-of-matter, so as to reduce the content of cyanuric acid and thereby treat the chlorinated water.

9. The method of claim 8, further comprising:
monitoring said concentration of said cyanuric acid in said chlorinated water; and maintaining said flowing until said concentration of said cyanuric acid in said water reaches a value less than 100 ppm.

10. The method of claim 9, wherein the amidohydrolase enzymes covalently attached to said water-insoluble matrix include cyanuric acid amidohydrolase, and wherein an amount of said cyanuric acid amidohydrolase required to reach said value in one cubic meter of said water within a time period of 24 hours is at least 2.5 mg per one cubic meter of said water.

11. The method of claim 8, wherein the water treatment is effected during a time period of 20 hours or less.

12. The method of claim 8, wherein passing said water through said device is effected at a flow rate of at least 10 cubic meters per hour.

13. The method of claim 8, wherein said circulating water reservoir is for use by humans.

14. The method of claim 8, wherein said circulating water reservoir is selected from the group consisting of a pool, an artificial pond or lake, a swimming pool, a spa, a hot-tub, a whirlpool bath, a fountain and a waterslide.

* * * * *